US008093288B2

(12) United States Patent
Zhang et al.

(10) Patent No.: US 8,093,288 B2
(45) Date of Patent: Jan. 10, 2012

(54) GENIPIN DERIVATIVES AND USES THEREOF

(75) Inventors: Chen-Yu Zhang, Swampscott, MA (US); Bradford B. Lowell, Southborough, MA (US); John A Porco, Jr., Chestnut Hill, MA (US); Ruichao Shen, Boston, MA (US); Cheng T. Lin, Fresh Meadow, NY (US); Stefan Krauss, Cambridge, MA (US)

(73) Assignees: Beth Israel Deaconess Medical Center, Boston, MA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 12/622,296

(22) Filed: Nov. 19, 2009

(65) Prior Publication Data

US 2010/0168160 A1 Jul. 1, 2010

Related U.S. Application Data

(63) Continuation of application No. 11/241,768, filed on Sep. 29, 2005, now Pat. No. 7,649,014, which is a continuation of application No. PCT/US2004/009957, filed on Mar. 31, 2004.

(60) Provisional application No. 60/459,278, filed on Mar. 31, 2003.

(51) Int. Cl.
A61K 31/35 (2006.01)
A61K 31/352 (2006.01)
A61K 31/365 (2006.01)

(52) U.S. Cl. ........ 514/455; 514/309; 514/453; 514/454; 514/456; 514/457; 514/460

(58) Field of Classification Search .............. 514/27, 514/309, 453, 454, 455, 456, 457, 460
See application file for complete search history.

(56) References Cited

U.S. PATENT DOCUMENTS

| 4,410,710 | A | 10/1983 | Berkowitz et al. |
| 5,272,172 | A | 12/1993 | Fujii et al. |
| 5,674,498 | A | 10/1997 | Inoue et al. |
| 5,929,038 | A | 7/1999 | Chang |
| 5,994,577 | A | 11/1999 | Larsen et al. |
| 6,001,578 | A | 12/1999 | Lind et al. |
| 6,022,888 | A | 2/2000 | Morishige et al. |
| 6,162,826 | A | 12/2000 | Moon et al. |
| 6,225,478 | B1 | 5/2001 | Morishige et al. |
| 6,262,083 | B1 | 7/2001 | Moon et al. |
| 6,365,796 | B1 | 4/2002 | Lowell et al. |
| 6,608,040 | B1 | 8/2003 | Sung et al. |
| 6,624,138 | B1 | 9/2003 | Sung et al. |

FOREIGN PATENT DOCUMENTS

| JP | 02096587 | 4/1990 |
| JP | 3066682 | 3/1991 |
| JP | 05058859 | 3/1993 |
| JP | 5-178749 | 7/1993 |
| JP | 2535674 | 7/1996 |
| JP | 9-95445 | 4/1997 |
| JP | 9278777 | 10/1997 |
| WO | WO 92/06061 | 4/1992 |
| WO | WO 97/32868 | 9/1997 |
| WO | WO 98/19718 A1 | 5/1998 |
| WO | WO 99/23090 | 5/1999 |
| WO | WO 2004/012676 A2 | 2/2004 |

OTHER PUBLICATIONS

Fujikawa, S., et al., "Genipin, a New Type of Protein Crosslinking Reagent from Gardenia Fruits," *Agric. Biol. Chem.*, 52:(3)869-870 (1988).
Huang, L., et al., "Biocompatibility Study of a Biological Tissue Fixed with a Naturally Occurring Crosslinking Reagent," *Journal of Biomedical Materials Research*, 42(4):568-576 (1998).
Fujikawa, S., et al., "Structure of Genipocyanin $G_1$, A Spontaneous Reaction Product. Between Genipin and Glycine," *Tetrahedron Lett.*, 28(40):4699-4700 (1987).
Touyama, R., et al., "Studies on the Blue Pigments Produced From Genipin and Methylamine. II. On the Formation Mechanisms of Brownish-Red Intermediates Leading to the Blue Pigment Formation." *Chem. Pharm. Bull.*, 42(8):1571-1578 (1994).
Park, J.-E., et al., "Isolation and Characterization of Water-Soluble Intermediates of Blue Pigments Transformed from Geniposide of Gardenia Jasminoides," *J. of Agric. Food Chem.*, 50:6511-6514 (2002).
Bringmann, G., et al., "Gardenamide A from *Rothmannia urceliformis* (Rubiaceae)—Isolation, Absolute Stereostructure, and Biomimetic Synthesis from Genipin," *Eur. J. Org. Chem.*, 10(10):1983-1987 (2001).
Mansour, T. S., "Antiviral nucleosides," *Curr. Pharm. Design*, 3(2):227-264 (1997).
Nakatani, K., "Synthesis of Asperuloside Aglucon Silyl Ether and Garjasmine from (+)-Genipin via Gardenoside Aglucon Bis(silyl ether) as a Common Intermediate," *Bull. Chem. Soc. Jpn.*, 66(9): 2646-2652 (1993).
Miyagoshi, M., et al., "The Structural Transformation of Gardenoside and its Related Iridoid Compounds by Acid and β-Glucosidase," *Planta Medica*, 53(4):462-464, (1987).
Fujikawa, S., et al., "The Continuous Hydrolysis of Geniposide to Genipin Using Immobilized β-Glucosidase on Calcium Alginate Gel," *Biotech Letters*, 9(10):697-702 (1987).
Zhang, C.-Y., et al., "Uncoupling Protein-2 Negatively Regulates Insulin Secretion and is a Major Link Between Obesity, Beta Cell Dysfunction, and Type 2 Diabetes," *Cell*, 105(6):745-755 (2001).
Joseph, J. W ., et al., "Uncoupling Protein 2 Knockout Mice have Enhanced Insulin Secretory Capacity after a High-Fat Diet," *Diabetes*, 51:3211-3219 (2002).
Krauss, S., et al., "Superoxide-Mediated Activation of UCP2 Pancreatic B-Cell Disfunction," *J. Clin. Invest.* 112(12):1831-1842 (2003).
Djerassi, Carl, et al., "Terpenoids, XLVII. The Structure of Genipin," *J Am. Chem. Soc.* 26:1192- 1206 (1961).

(Continued)

*Primary Examiner* — Bernard Dentz
(74) *Attorney, Agent, or Firm* — Hamilton, Brook, Smith & Reynolds, P.C.

(57) ABSTRACT

Genipin derivatives and pharmaceutical compositions thereof that inhibit the activity of uncoupling protein-2 (UCP2) and are useful in treating deficient first-phase insulin secretion, non-insulin dependent diabetes mellitus, and ischemia in a mammal are disclosed.

14 Claims, 9 Drawing Sheets

OTHER PUBLICATIONS

Sang, S., et al., "Chemical Components in Noni Fruits and Leaves (*Morinda citrifolia* L.)," *ACS Symposium Series (220)* 803 (*Quality Management of Nutraceuticals*), 134-150 (2002).

Li, J., et al., "Determination of Loganin in Jiangtangqing capsules by RP-HPLC," *Zhongccaoyao Zazhi Bianjibu*, 30(1 1):820-822 (1999).

Kimura, Y., et al., "Effects of Geniposide Isolated from *Gardenia jasminoides* on Metabolic Alterations in High Sugar Diet-fed Rats," *Chem. Pharm. Bull.*, 30(12):4444-4447 (1982).

Aungst, Jr., R.A., et al., "Synthesis of (Z) -2-Acyl-2-enals via Retrocycloadditions of 5-Acyl-4-alkyl-4*H*-1, 3-dioxins: Application in the Total Synthesis of the Cytotoxin (±)-Euplotin A," *J. Am. Chem. Soc.*, 123(38):9455-9456 (2001).

Ge, Y. -t., et al., "Absolute Configuration of Novel Marine Diterpenoid Udoteatrial Hydrate Synthesis and Cytotoxicities of *ent*-Udoteatrial Hydrate and Its Analogs," *Tetrahedron*, 49(46):10555-10576 (1993).

Ge, Y., et al., "Synthesis of The Antipode of Udoteatrial Hydrate Using (+)-Genipin as a Chiral Building Block: Determination of the Absolute Configuration of Udoteatrial Hydrate," *Tetrahedron Letters*, 34(16):2621-2624 (1993).

Inoue, K., et al., "Studies on Monoterpene Glucosides and Related Natural Products. XLI. Chemical Conversion of Geniposide into 10-Hydroxyloganin," *Chem. Pharm. Bull.*, 29(4):970-980 (1981).

Inouye, H., et al., "Monoterpeneglucosides and related natural compounds. XX. Structure of forsythid, a new iridoid glucoside of *Forsythia viridissima*," *Chem. Pharm. Bull.*, 21(3):497-502 (1973).

Kawata, Y., et al., "Formation of Nitrogen-Containing Metabolites from Geniposide and Gardenoside by Human Intestinal Bacteria," *Planta Med.*, 57(6):536-542 (1991).

Miyagoshi, M., et al., "Choleretic Actions of Iridoid Compounds," *J. Pharmacohio-Dyn.*, 11:186-190 (1988).

Isiguro, K., et al., "Studies on Iridoid-Related Compounds. IV. Antitumor Activity of Iridoid Aglycones," *Chem. Pharm. Bull.*, 34(6):2375-2379 (1986).

Ishiguro, K., et al, "Studies on lridoid-Related Compounds, II. The Structure and Antimicrobial Activity of Aglucones of Galioside and Gardenoside," *Journal of Natural Products*, 46(4):532-536 (1983).

Berkowitz, W. F., et al., "Conversion of Asperuloside to Optically Active Prostaglandin Intermediates," *Journal of Organic Chemistry*, 47(5):824-829 (1982).

Berkowitz, W. F., et al., "The Conversion of Asperuloside to an Optically Active Prostaglandin Intermediate," *Tetrahedron Letters*, 22(12):1075-1076 (1981).

Kocsis, et al., "Synthetic Modification of Iridoids to Non-natural Indole Alkaloids," *Biodiversity: Biomolecular Aspects of Biodiversity and Innovative Utilization, Sener, B., Ed.*; Kluwer Academic/Plenum New York 375-377 (2002).

Porte, Jr., D., "Clinical Importance of Insulin Secretion and its Interaction With Insulin Resistance in the Treatment of Type 2 Diabetes Mellitus and its Complications," *Diabetes Metab Res Rev*, 17:181-188 (2001).

Valsecchi, G., et al., "Increased Nitric Oxide Levels and First-Phase Insulin Secretion are Early Features of Diet-Induced Insulin Resistance in Rats," *Diabetologia, 42 (Suppl. 1)*: A141 (1999). Abstract No. 522.

Letiexhe, M. R., et al., "Comparative Evaluation of Simple Indices Based on Fasting Plasma Insulin to Assess Insulin Sensitivity," *Diabetologia, 42 (Suppl. 1)*: A186 (1999). Abstract No. 693.

Scheffler, I. E., "Mitochondrial Electron Transport and Oxidative Phosphorylation," In *Mitochondria*, (NY: Wiley-Liss), pp. 141-245 (1999).

Fleury, C., et al., "Uncoupling Protein-2: A Novel Gene Linked to Obesity and Hyperinsulinemia," *National Genetics*, 15:269-272 (1997).

Gimeno, R.E., et al., "Cloning and Characterization of an Uncoupling Protein Homolog,"*Diabetes*, 46(5):900- 905 (1997).

Boss, O., et al., "Uncoupling Protein-3: A New Member of the Mitochondrial Carrier Family with Tissue-Specific Expression," *FEBS Letters*, 408.. 39-42 (1997).

Vidal-Puig, A., et al., "UCP3: An Uncoupling Protein Homologue Expressed Preferentially and Abundantly in Skeletal Muscle and Brown Adipose Tiddue," *Biochemical and Biophysical Research Communications*, 235: 79-82 (1997).

Gong, D.W., et al., Uncoupling Protein-3 Is a Mediator of Thermogenesis Regulated by Thyroid Hormone, β3-Adrenergic Agonists, and Leptin, *The Journal of Biological Chemistry*, 272(39) :24129-24132 (1997).

Nicholls, D.G., et al., Thermogenic Mechanisms in Brown Fat, *The American Physiological Society*, 641(1): 1-64 (1984).

Klingenberg, M., and Huang, S.G., Structure and Function of the Uncoupling Protein From Brown Adipose Tissue, *Biochimica et Biophysica Acta*,, 1415: 271-296 (1999).

Zhou, Y.T., et al, Induction By Leptin of Uncoupling Protein-2 and Enzymes of Fatty Acid Oxidation, *Proceedings of the National Academy of Sciences of the United States of America*, 94: 6386-6390 (1997).

Chan, C.B., et al., Overexpression of Uncoupling Protein 2 Inhibits Glucose-Stimulated Insulin From Rat Islets, *Diabetes 48*: 1-5 (1999).

Rial, E., et al., Retinoids Activate Proton Transport by the Uncoupling Proteins UCP1 and UCP2, *EMBO Journal*, 18 (21): 5827-5833 (1999).

Hinz, W., et al., Recombinant Human Uncoupling Protein-3 Increases Thermogenesis in Yeast Cells, *FEBS Letters*, 448: 57-61 (1999).

Zhang, C. Y., et al., Assessment of Uncoupling Activity of Uncoupling Protein 3 Using a Yeast Heterologous Expression System, *FEBS Letters*, 449: 129-134 (1999).

Jaburek, M., et al., "Transport Function and Regulation of Mitochondrial Uncoupling Proteins 2 and 3," *Journal of Biological Chemistry*, 274 (37): 26003-26007 (1999).

Seldin, M.F., et al., "Glycogen Synthase: A Putative Locus for Diet-induced Hyperglycemia," *Journal of Clinical Investigation*, 94: 269-276 (1994).

Gauguier, D., et al., "Chromosomal Mapping of Genetic Loci Associated With Non-Insulin Dependent Diabetes in the GK Rat," *Nature Genetics*, 12: 38-43 (1996).

Galli, J., et al., "Genetic Analysis of Non-Insulin Dependent Diabetes Mellitus in the GK Rat," *Nature Genetics*, 12: 31-37 (1996).

Kaisaki, P.J., et al., "Localization of *Tub* and Uncoupling Proteins (*Ucp*) 2 and 3 to a Region of Rat Chromosome 1 Linked to Glucose Intolerance and Adiposity in the Goto-Kakizaki (GK) Type 2 Diabetic Rat," *Mammalian Genome*, 9: 910-912 (1998).

Echtay, et al., "Superoxide Activates Mitochondrial Uncoupling Proteins," *Nature*, 415: 96-99 (2002).

Cawthorn, E. G. and Chan, B. C., "Effect of Pertussis Toxin on Islet Insulin Secretion in Obese (*fa/fa*) Zucker Rats," *Molecular and Cellular Endocrinology*, 75: 197-204 (1991).

Miura, T., et al., "Hypoglycemia Activity and Structure-Activity Relationship of Iridoidal Glycosides," *Pharmaceutical Society of Japan*, 19(1): 160-161 (1996).

Franzyk, H., et al., "Iridoid Glucosides From *Penstemon secundiflorus* and *P. grandiflorus*: Revised Strucure of 10-Hydroxy-8-Epihastatoside," *Phytochemistry*, 49(7): 2025-2030 (1998).

Teborg, D., et al., "Iridoid Glucosides From Penstemon Nitidus Iridoid Glucosides," *Planta Medica*, 57(2): 184-190 (1991).

Jensen, S. R., et al., "Dihydrocornin, A Novel Natural Iridoid Glucoside," *Acta Chemica Scandinavica*, 27(7): 2581-2586 (1973).

Chang, C., et al., "Bicyclo '3.2.1! octenones as Building Blocks in Natural Products Synthesis. 2 Formal Synthesis of (.+–.)-Verbenalol," *Journal of Organic Chemistry*, 59(7): 1898-1907 (1994).

Laabassi, M., et al., "Total Synthesis of (−)-verbenalol and (−)-epiverbenalol," *Tetrahedron Letters*, 29(6): 611-625 (1988).

Misra, A. P., et al., "Modified Iridoid Glycosides as Anti-Implantation Agents: Inhibition of Cell Adhesion as an Approach for Developing Pregnancy Interceptive Agents," *Bioorganic & Medicinal Chemistry*, 9(11): 2763-2772 (2001).

Nangia A., et al., "Synthesis of Cyclopenta 'c!pyran Skeleton of Iridoid Lactones," *Tetrahedron, Elsevier Science Publishers*, 53(43): 14507-14545 (1997).

U.S. Appl. No. 11/241,768, Oct. 25, 2006, Office Action—Restriction.

U.S. Appl. No. 11/241,768, Dec. 21, 2006, Reply to Restriction Requirement.

U.S. Appl. No. 11/241,768, Jan. 23, 2007, Office Action—Restriction.
U.S. Appl. No. 11/241,768, Mar. 14, 2007, Reply to Restriction Requirement and Preliminary Amendment.
U.S. Appl. No. 11/241,768, Jul. 3, 2007, Office Action—Restriction.
U.S. Appl. No. 11/241,768, Aug. 3, 2007, Reply to Restriction Requirement.
U.S. Appl. No. 11/241,768, Oct. 22, 2007, Office Action—Restriction.
U.S. Appl. No. 11/241, 768, Feb. 21, 2008, Reply to Restriction Requirement and Second Preliminary Amendment.
U.S. Appl. No. 11/241,768, Jun. 9, 2008, Office Action.
U.S. Appl. No. 11/241,768, Dec. 8, 2008, Amendment.
U.S. Appl. No. 11/241,768, Mar. 10, 2009, Office Action (Final).
U.S. Appl. No. 11/241,768, Aug. 10, 2009, Amendment After Final.
U.S. Appl. No. 11/241,768, Aug. 27, 2009, Interview Summary and Supplemental Amendment After Final.
U.S. Appl. No. 11/241,768, Sep. 4, 2009, Notice of Allowance.

Ling, S.K., et al., "Effects of Iridoids on Lipoxygenase and Hyaluronidase Activities and Their Activation by β-glucosidase in the Presence of Amino Acids," *Biological & Pharmaceutical Bulletin*, 26(3):352-356 (2003).
Calis, I., et al., "Iridoid Glycosides from Globularia Davisiana," *Chemical & Pharmaceutical Bulletin*, 50(5):678-680 (2002).
Vieira, I.J.C., et al., "Iridoids from *Borreria verticillata*," *Organic Letters*, 1(8):1169-1171 (1999).
Kraus and Thurston, "A Direct Synthesis of Hydroxysemperoside Deglucoside," *Journal of the American Chemical Society*, 111(26):9203-5 (1989).
Inouye, H., et al., "Studies on Monoterpene Glucosides and Related Natural Products. Part 61. Chemotaxonomic Studies of Rubiaccous Plants Containing Iridoid Glycosides," *Phytochemistry* 27(8):2591-2598 (1988).
Isiguro, K., et al., "Studies on Iridoid-Related Compounds. IV. Antitumor Activity of Iridoid Aglycones," *Chemical & Pharmaceutical Bulletin*, 34(6):2375-9 (1986).
Jensen, S.R., "Iridoids in Rothmannia Globosa," *Phytochemistry (Elsevier)*, 22(8):1761-5 (1983).

Proton leak titration in kidney mitochondria from wildtype and UCP2 KO mice

Figs. 11A, 11B, and 11C

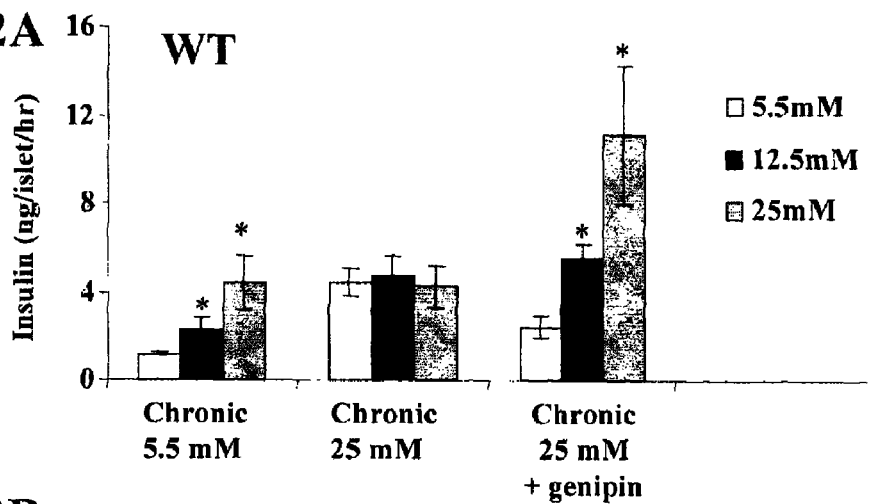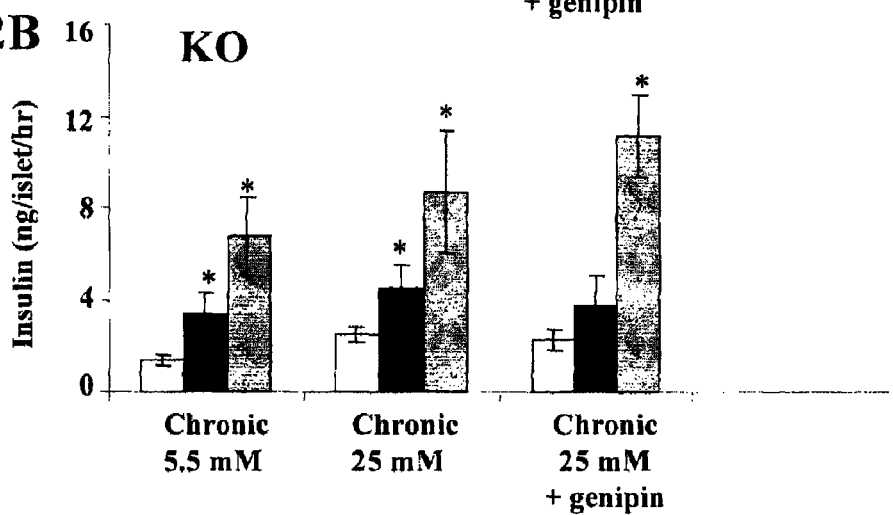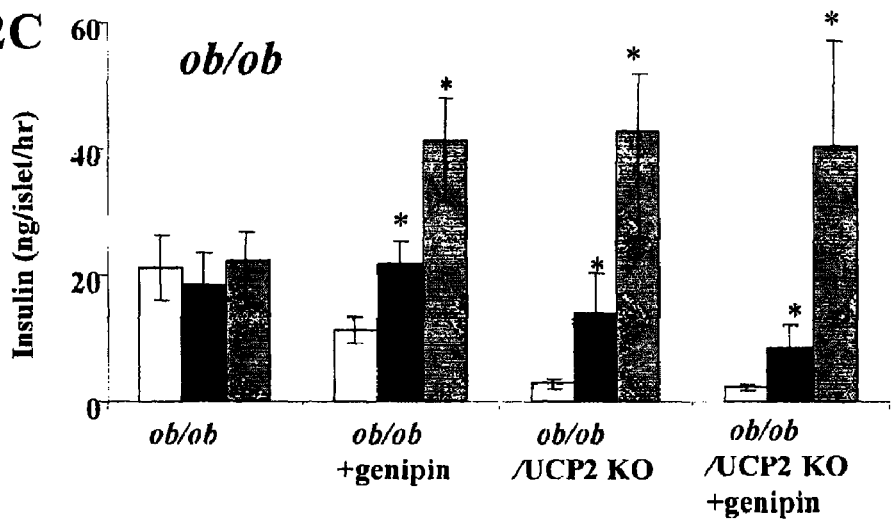
Figs 12A, 12B, and 12C

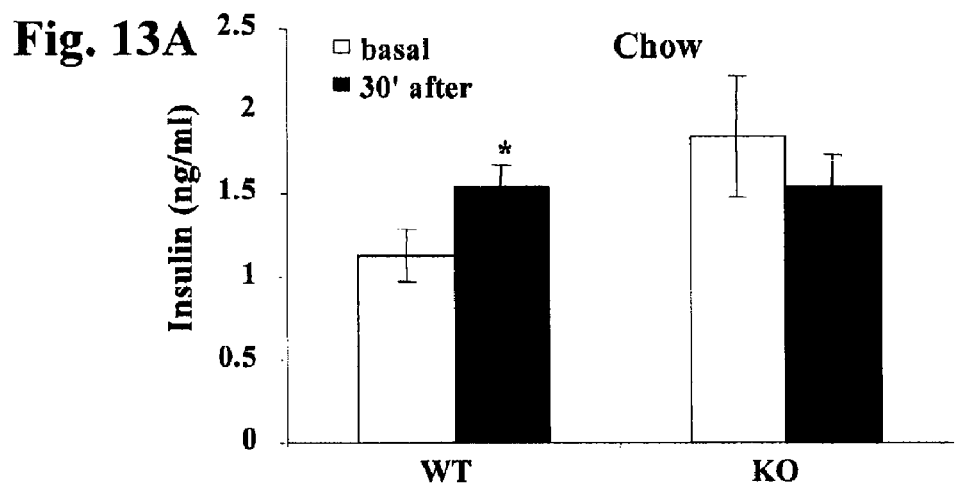
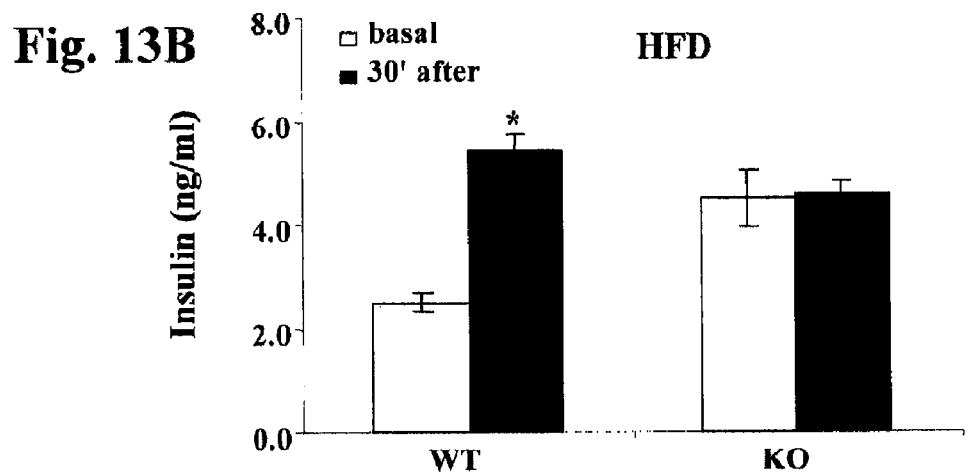
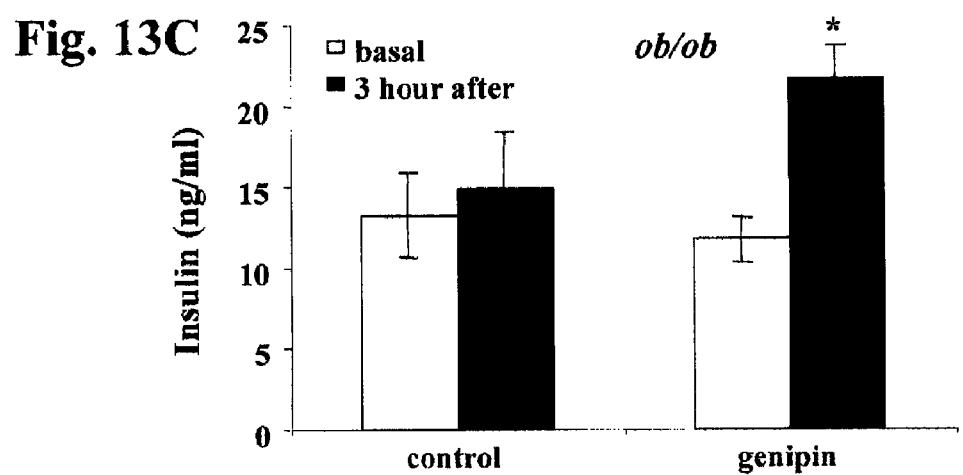
Figs 13A, 13B, and 13C

GENIPIN DERIVATIVES AND USES THEREOF

RELATED APPLICATIONS

This application is a continuation of U.S. application Ser. No. 11/241,768, filed on Sep. 29, 2005 now U.S. Pat. No. 7,649,014, which is a continuation of International Application No. PCT/US2004/009957, filed on Mar. 31, 2004, which claims the benefit of U.S. Provisional Application No. 60/459,278, filed on Mar. 31, 2003. The entire teachings of the above applications are incorporated herein by reference.

GOVERNMENT SUPPORT

The invention was supported, in whole or in part, by a grant R01 DK53477 from National Institutes of Health. The Government has certain rights in the invention.

BACKGROUND OF THE INVENTION

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. Type II diabetes mellitus (also known as non-insulin dependent diabetes) is the form of diabetes which is due to a profound resistance to insulin stimulating or regulatory effect on glucose metabolism in the main insulin-sensitive tissues (muscle, liver and adipose tissue) which occurs in association with relative β cell dysfunction.

Current treatment for diabetes mellitus generally first involves treatment with diet and exercise. However, compliance can be poor and as the disease progresses treatment with hypoglycemics, typically sulfonylureas, thiazolidinediones, or metformin, is often necessary. However, in many patients, these pharmaceutical agents prove inadequate for maintaining blood glucose at an acceptable level and injection with insulin is necessary. Since insulin injection has the life threatening side effect of hypoglycemic coma, patients using insulin injections must carefully control dosage.

Therefore, a need exists for new pharmaceutical agents which prevent, treat and/or alleviate diabetes and related complications of the disease without imposing on the patient burdensome and complicated treatment regimes which may effect patient compliance.

SUMMARY OF THE INVENTION

The present invention is directed to compounds and pharmaceutical compositions that inhibit the activity of uncoupling protein-2 (UCP2) and are useful for the treatment of diseases or conditions where increased activity of UCP2 contributes to the cause of the disease or condition. Examples of diseases or conditions that involve increased activity of UCP2 in a mammal include deficient first-phase insulin secretion, non-insulin dependent diabetes mellitus, and ischemia (e.g., ischemia reperfusion disease). Compounds of the invention are derivatives of genipin, a component of gardenia extract. As will be shown below, one cause of β-cell dysfunction is increased UCP2 activity which inhibits insulin secretion. Genipin works by directly attacking this cause of β-cell dysfunction by inhibiting UCP2 activity. Compounds currently used to treat non-insulin dependent diabetes mellitus have either unknown mechanisms of action (e.g., metformin) or increase PPAR-gamma-mediated gene transcription (e.g., thiazolidinediones), a process that has not been shown to be impaired in diabetes mellitus.

Compounds which can be employed in methods of the invention include those represented by structural formula A:

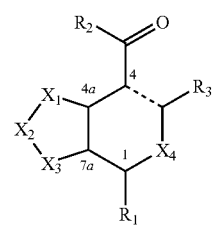

or pharmaceutically acceptable salts thereof. In Structural Formula A:

— — — — is a single or double bond.

$X_1$ is $=CR_{18}$—, $X_2$ is $=CR_{12}$—, and $X_3$ is $CR_{13}R_{14}$; $X_2$ is $=CR_{18}$—, $X_3$ is $=CR_{12}$—, and $X_1$ is $CR_{13}R_{14}$; or $X_1$ is $CR_6R_7$, $X_2$ is $CR_8R_9$ and $X_3$ is $CR_{10}R_{11}$.

$X_4$ is —O— or —NR—.

Each R is independently H or a C1-C5 alkyl.

$R_1$ is —H, —OH, =O, —OSi$(R_{19})_3$, a hexose or pentose; or R1, taken together with a substituent of $X_3$ selected from $R_{10}$, $R_{11}$, $R_{12}$, $R_{13}$, $R_{14}$, and $R_{18}$, together with C7a, the carbon to which $R_1$ is attached, and the carbon represented by $X_3$, form a cyclic ether. In various embodiments, the cyclic ether can form a 6-7 membered ring, or typically a 5 membered ring.

$R_2$ is —OR, or —NR$_4$R$_5$; or when $X_1$ is $CR_{13}R_{14}$, $R_2$ and $R_{13}$, together with C4, C4a, the carbon to which $R_{13}$ is attached and the carbonyl group to which $R_2$ is attached, form a lactone ring. In various embodiments, the cyclic ether can form a 6-7 membered ring, or typically a 5 membered ring.

$R_3$ is —H, —OH, or —OR, or, optionally when — — — — is a single bond, =O.

$R_4$ and $R_5$ are each, independently, —H or a C1-C5 alkyl; or $R_4$ and $R_5$ together with the nitrogen to which they are attached form a heterocyclic ring, wherein the C1-C5 alkyl or the heterocyclic ring are optionally substituted with one or more of hydroxy, a halo, a C1-C5 alkyl, phenyl, or cyano.

$R_6$, $R_7$, $R_8$, $R_9$, $R_{10}$, $R_{11}$, $R_{13}$, $R_{14}$ and $R_{99}$ are independently —H, —OH, —F, —Cl, —Br, —I, —NO$_2$, —NR$_2$, —C(O)NR$_2$, a C1-C5 alkyl, a hydroxyalkyl, —CH$_2$OC(O) NR$_{15}$R$_{16}$, or —CH$_2$OC(O)R$_{17}$; or $R_{13}$ and $R_{14}$ together are =O; or $R_8$ and $R_{10}$ together with two adjacent carbons to which they are attached, form an epoxy ring; or $R_6$ and $R_8$ together with two adjacent carbons to which they are attached, form an epoxy ring.

$R_{12}$ and $R_{18}$ are each, independently, —H, a C1-C5 alkyl, hydroxyalkyl, —CH$_2$OC(O)NR$_{15}$R$_{16}$, —CH$_2$OC(O)R$_{17}$, or —CH$_2$OH.

$R_{15}$ and $R_{16}$ are each, independently, —H or a C1-C5 alkyl.

$R_{17}$ is a C1-C5 alkyl.

$R_{19}$ for each occurrence is, independently, a C1-C5 alkyl or an aryl.

Additional compounds and pharmaceutical compositions of the invention can be represented by structural formula I, and pharmaceutically acceptable salts thereof:

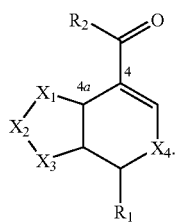

I

In structural formula I, $X_1$ is $=CR_{18}-$, $X_2$ is $=CR_{12}-$, and $X_3$ is $CR_{13}R_{14}$; $X_2$ is $=CR_{18}-$, $X_3$ is $=CR_{12}-$, and $X_1$ is $CR_{13}R_{14}$; or $X_1$ is $CR_6R_7$, $X_2$ is $CR_8R_9$ and $X_3$ is $CR_{10}R_{11}$. $X_4$ is $-O-$ or $-NR-$. R is H or a C1-C5 alkyl. $R_1$ is $-OH$, $=O$, $-OSi(R_{19})_3$, a hexose or pentose. $R_2$ is $-OR$, or $-NR_4R_5$; or when $X_1$ is $CR_{13}R_{14}$, $R_2$ and $R_{13}$, together with C4, C4a, C5, the carbon to which $R_{13}$ is attached and the carbonyl group to which $R_2$ is attached, form a five membered lactone ring. $R_4$ and $R_5$ are each, independently, $-H$ or a C1-C5 alkyl; or $R_4$ and $R_5$ together with the nitrogen to which they are attached form a heterocyclic ring, wherein the C1-C5 alkyl or the heterocyclic ring are optionally substituted with one or more substituents selected from the group consisting of hydroxy, a halo, a C1-C5 alkyl, phenyl, and cyano. $R_6$, $R_7$, $R_8$, $R_9$, $R_{10}$, $R_{11}$, $R_{13}$ and $R_{14}$ are each, independently, selected from the group consisting of $-H$, $-OH$, a C1-C5 alkyl, a hydroxyalkyl, $-CH_2OC(O)NR_{15}R_{16}$, $-CH_2OC(O)R_{17}$, or $-CH_2OH$; or $R_{13}$ and $R_{14}$ together are $=O$; or $R_8$ and $R_{10}$ together with two adjacent carbons to which they are attached, form an epoxy ring. $R_{12}$ and $R_{18}$ are each, independently, $-H$, a C1-C5 alkyl, hydroxyalkyl, $-CH_2OC(O)NR_{15}R_{16}$, $-CH_2OC(O)R_{17}$, or $-CH_2OH$. $R_{15}$ and $R_{16}$ are each, independently, $-H$ or a C1-C5 alkyl. $R_{17}$ is a C1-C5 alkyl. $R_{19}$ for each occurrence is, independently, a C1-C5 alkyl or an aryl.

However, when compounds represented by formula A or I are used to treat the late stages of non-insulin dependent diabetes mellitus, the variables are as defined above provided that when $X_4$ is $-O-$, $R_2$ is $-OCH_3$, and $R_1$ is $=O$, $-OH$, $-OC(O)CH_3$, glucosyl, O-tetraacetylglucosyl, O-tetramethylglucosyl, or t-butyldimethylsiloxy, and $X_3$ is $=CR_{12}$ or $CR_{10}R_{11}$, none of $R_{10}$, $R_{11}$, or $R_{12}$ is $-CH_2OH$, $-CH_2OC(O)CH_3$, or $-CH_3$; when $X_4$ is $-O-$, $R_2$ is $-OCH_3$, and $R_1$ is $-H$, $=O$, $-OH$ or t-butyldimethylsiloxy, and $X_3$ is $CR_{10}R_{11}$, none of $R_{10}$ and $R_{11}$ is $-CH_2OH$, and $R_{10}$ and $R_{11}$ are not both $-H$; and the compound is not represented by Structural Formula B:

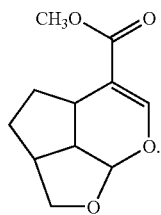

B

In some embodiments, the variables are as defined above provided that when $X_4$ is $-O-$, $R_2$ is $-OR$, and $R_1$ is $=O$, $-OH$, $-OC(O)R_{17}$, hexose, or t-butyldimethylsiloxy, and $X_3$ is $=CR_{12}$ or $CR_{10}R_{11}$, none of $R_{10}$, $R_{11}$, or $R_{12}$ is $-OH$, hydroxyalkyl, $-CH_2OC(O)R_{17}$, or alkyl; when $X_4$ is $-O-$, $R_2$ is $-OR$, and $R_1$ is $-H$, $=O$, $-OH$ or t-butyldimethylsiloxy, and $X_3$ is $CR_{10}R_{11}$, none of $R_{10}$ and $R_{11}$ is $-OH$ or hydroxyalkyl, and $R_{10}$ and $R_{11}$ are not both $-H$; and the compound is not represented by Structural Formula B.

Also, when compounds represented by formula A or I are used to treat ischemia, the variables are as defined above provided that when X4 is $-O-$; R1 is a hexose or $-OH$; and $X_2$ is $=CR_{18}-$, $X_3$ is $=CR_{12}-$, and $X_1$ is $CR_{13}R_{14}$, or $X_1$ is $CR_6R_7$, $X_2$ is $CR_8R_9$ and $X_3$ is $CR_{10}R_{11}$, none of $R_{10}$, $R_{11}$, and $R_{12}$ is $-CH_2OH$. In some embodiments, the variables are as defined above provided that when X4 is $-O-$; R1 is a hexose, $=O$, or $-OH$; and $X_2$ is $=CR_{18}-$, $X_3$ is $=CR_{12}-$, and $X_1$ is $CR_{13}R_{14}$, or $X_1$ is $CR_6R_7$, $X_2$ is $CR_8R_9$ and $X_3$ is $CR_{10}R_{11}$, none of $R_{10}$, $R_{11}$, and $R_{12}$ is $-OH$ or hydroxyalkyl.

Compounds of the invention and compounds employed in the pharmaceutical composition of the invention can be represented by Structural Formula A, or pharmaceutically acceptable salts thereof, wherein the variables are further defined as set forth in the following embodiments.

In some embodiments, $R_1$ is $-H$, $-OH$, $=O$, $-OSi(R_{19})_3$, a hexose or pentose; $X_1$ is $CR_{13}R_{14}$; and $R_2$ and $R_{13}$, together with C4, C4a, the carbon to which $R_{13}$ is attached and the carbonyl group to which $R_2$ is attached, form a lactone ring. In some embodiments, $R_1$, taken together with a substituent of $X_3$ selected from $R_{10}$, $R_{11}$, $R_{12}$, $R_{13}$, $R_{14}$, and $R_{18}$, together with C7a, the carbon to which $R_1$ is attached, and the carbon represented by $X_3$, form a cyclic ether; and $R_2$ is $-OR$ or $-NR_4R_5$. In still other embodiments, $R_1$, taken together with a substituent of $X_3$ selected from $R_{10}$, $R_{11}$, $R_{12}$, $R_{13}$, $R_{14}$, and $R_{18}$, together with C7a, the carbon to which $R_1$ is attached, and the carbon represented by $X_3$, form a cyclic ether; $X_1$ is $CR_{13}R_{14}$; and $R_2$ and $R_{13}$, together with C4, C4a, the carbon to which $R_{13}$ is attached and the carbonyl group to which $R_1$ is attached, form a lactone ring;

When compounds represented by formula A are claimed as compounds, the variables are as defined above provided that:
when $X_4$ is $-O-$, $R_2$ is $-OCH_3$, and $R_1$ is $=O$, $-OH$, $-OC(O)CH_3$, glucosyl, O-tetraacetylglucosyl, O-tetramethylglucosyl, or t-butyldimethylsiloxy, and $X_3$ is $=CR_{12}$ or $CR_{10}R_{11}$, none of $R_{10}$, $R_{11}$, or $R_{12}$ is $-CH_2OH$, $-CH_2OC(O)CH_3$, or $-CH_3$.
when $X_4$ is $-NR-$, $R_2$ is $-OCH_3$, and $R_1$, taken together with a substituent of $X_3$ selected from $R_{13}$, and $R_{14}$, together with C7a, the carbon to which $R_1$ is attached, and the carbon represented by $X_3$, form the cyclic ether; none of $R_{13}$ and $R_{14}$ is $-OH$.
when $X_1$ is $CR_6R_7$, $X_2$ is $CR_8R_9$ and $X_3$ is $CR_{10}R_{11}$, the cyclic ether is unsubstituted, and R8, R9, and R11 are independently $-F$, $-Cl$, $-Br$, $-I$, $-NO_2$, $-NR_2$, $-C(O)NR_2$, a C1-C5 alkyl, or $-CH_2OC(O)NR_{15}R_{16}$.
when X4 is $-O-$; R1 is a hexose or $-OH$; and $X_2$ is $=CR_{18}-$, $X_3$ is $=CR_{12}-$, and $X_1$ is $CR_{13}R_{14}$, or $X_1$ is $CR_6R_7$, $X_2$ is $CR_8R_9$ and $X_3$ is $CR_{10}R_{11}$, none of $R_{10}$, $R_{11}$, and $R_{12}$ is $-CH_2OH$; and
the compound is not represented by Structural Formula B.
In other embodiments, when compounds represented by formula A are claimed as compounds, the variables are as defined above provided that:
when $X_4$ is $-O-$, $R_2$ is $-OR$, and $R_1$ is $=O$, $-OH$, $-OC(O)R_{17}$, hexose, or t-butyldimethylsiloxy, and $X_3$ is $=CR_{12}$ or $CR_{10}R_{11}$, none of $R_{10}$, $R_{11}$, or $R_{12}$ is $-OH$, hydroxyalkyl, $-CH_2OH$, $-CH_2OC(O)R_{17}$, or alkyl.
when $X_4$ is $-NR-$, $R_2$ is $-OR$, and $R_1$, taken together with a substituent of $X_3$ selected from $R_{13}$, and $R_{14}$, together with C7a, the carbon to which $R_1$ is attached, and the carbon represented by $X_3$, form the cyclic ether; none of $R_{13}$ and $R_{14}$ is $-OH$ or hydroxyalkyl.

when $X_1$ is $CR_6R_7$, $X_2$ is $CR_8R_9$ and $X_3$ is $CR_{10}R_{11}$, the cyclic ether is unsubstituted, and R8, R9, and R11 are independently —F, —Cl, or —Br.

when X4 is —O—; R1 is a hexose, =O, or —OH; and $X_2$ is $=CR_{18}$—, $X_3$ is $=CR_{12}$—, and $X_1$ is $CR_{13}R_{14}$, or $X_1$ is $CR_6R_7$, $X_2$ is $CR_8R_9$ and $X_3$ is $CR_{10}R_{11}$, none of $R_{10}$, $R_{11}$, and $R_{12}$ is —OH or hydroxyalkyl; and the compound is not represented by Structural Formula B.

In another embodiment, the invention is directed to compounds and pharmaceutical compositions that inhibit the activity of uncoupling protein-2 (UCP2) and are useful in treating deficient first-phase insulin secretion, non-insulin dependent diabetes mellitus, or ischemia reperfusion disease in a mammal and can be represented by structural formula II, and pharmaceutically acceptable salts thereof:

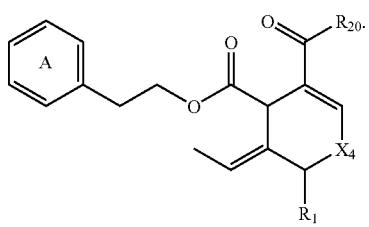

II

In structural formula II, $R_1$ and $X_4$ are defined as in structural formula I. Ring A is optionally substituted with one or more substituents selected from the group consisting of —OH, a halo, nitro, cyano, and carboxy. $R_{20}$ is —OR or —$NR_4R_5$. $R_4$ and $R_5$ are defined as above. In one embodiment, when $R_1$ is glucosyl, Ring A is not a 3,4-dihydroxyphenyl in compounds of the invention.

In another embodiment, the invention is directed to compounds and pharmaceutical compositions that inhibit the activity of uncoupling protein-2 (UCP2) and are useful in treating deficient first-phase insulin secretion, non-insulin dependent diabetes mellitus, or ischemia reperfusion disease in a mammal and can be represented by structural formula III, and pharmaceutically acceptable salts thereof:

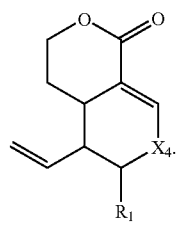

III

In structural formula III, $R_1$ and $X_4$ are defined as in structural formula I. In one embodiment, when $X_4$ is —O—, $R_1$ is not glucosyl in compounds of the invention.

In another embodiment, the invention is directed to compounds and pharmaceutical compositions that inhibit the activity of uncoupling protein-2 (UCP2) and are useful in treating deficient first-phase insulin secretion, non-insulin dependent diabetes mellitus, or ischemia reperfusion disease in a mammal and can be represented by structural formula IV, and pharmaceutically acceptable salts thereof:

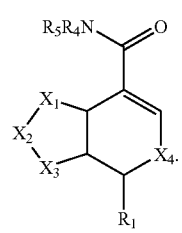

IV

In structural formula IV, $R_1$, $R_4$, $R_5$, and $X_4$ are defined as in structural formula I. $X_5$ is $=CR_{18}$—, $X_2$ is $=CR_{12}$—, and $X_3$ is $CR_{13}R_{14}$; $X_2$ is $=CR_{18}$—, $X_3$ is $=CR_{12}$—, and $X_5$ is $CR_{21}R_{22}$; or $X_1$ is $CR_6R_7$, $X_2$ is $CR_8R_9$ and $X_3$ is $CR_{10}R_{11}$, $R_6$, $R_7$, $R_8$, $R_9$, $R_{10}$, $R_{11}$, $R_{12}$, $R_{13}$, $R_{14}$ and $R_{18}$ are defined as above. $R_{21}$ and $R_{22}$ are each, independently, selected from the group consisting of —H, —OH, a C1-C5 alkyl, a hydroxyalkyl, —$CH_2OC(O)NR_{15}R_{16}$, —$CH_2OC(O)R_{17}$, or —$CH_2OH$; or $R_{21}$ and $R_{22}$ together are =O. $R_{15}$, $R_{16}$, $R_{17}$, $R_{19}$ are defined as above.

In another embodiment, the invention is directed to compounds and pharmaceutical compositions that inhibit the activity of uncoupling protein-2 (UCP2) and are useful in treating deficient first-phase insulin secretion, non-insulin dependent diabetes mellitus, or ischemia reperfusion disease in a mammal and can be represented by structural formula V, and pharmaceutically acceptable salts thereof:

V

In structural formula V, $R_1$, $R_2$ and $X_4$ are defined as in structural formula I. $R_{23}$, $R_{24}$, $R_{25}$, $R_{26}$ are each, independently, selected from the group consisting of —H, —OH, a C1-C5 alkyl, a hydroxyalkyl, —$CH_2OC(O)NR_{15}R_{16}$, —$CH_2OC(O)R_{17}$, or —$CH_2OH$. $R_{15}$, $R_{16}$, $R_{17}$, and $R_{19}$ are defined as above. In one embodiment, when $R_1$ is glucosyl and $R_{25}$ is —H, $R_{26}$ is not methyl in compounds of the invention.

BRIEF DESCRIPTION OF THE DRAWINGS

FIGS. 12A, 12B, and 12C are bar graphs showing effects of hyperglycemia and obesity on in vitro β-cell dysfunction in WT and UCP2-deficient islets, with or without 5 mM genipin.

FIGS. 13A, 13B, and 13C are bar graphs showing the effects of genipin on insulin secretion in vivo.

DETAILED DESCRIPTION OF THE INVENTION

Figure 1:
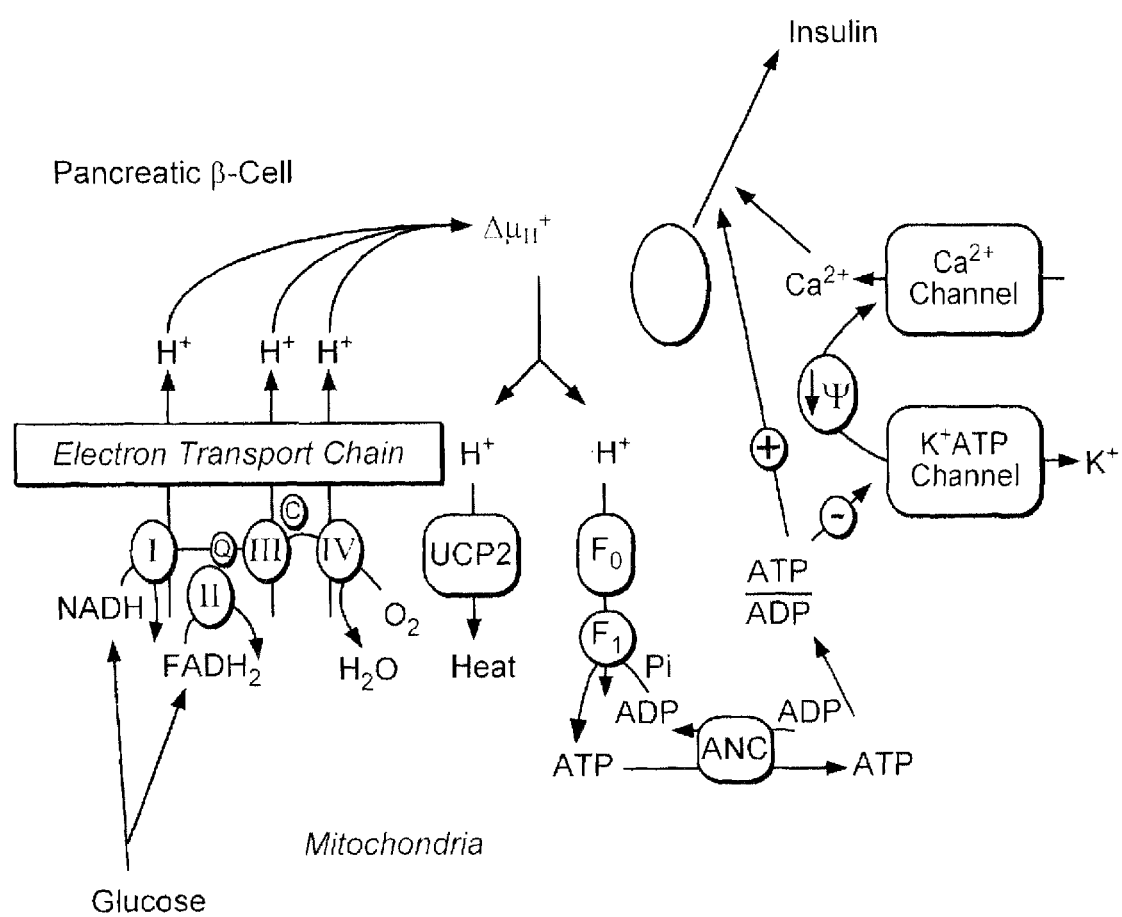
FIG. 1 is a schematic representation of the oxidative metabolism of glucose.

The term "alkyl" as used herein means straight-chain, branched or cyclic hydrocarbons which are completely saturated. For example, suitable aliphatic groups include substituted or unsubstituted linear, branched or cycloalkyl groups and hybrids thereof such as (cycloalkyl)alkyl. Preferably, straight-chained and branched alkyl groups have from one to five carbon atoms and cycloalkyl groups have from three to seven carbon atoms.

The term "halo" means F, Cl, Br or I.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-napthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthriidinyl, or tetrahydronaphthyl, where the radical or point of attachment is on the aromatic ring.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR (as in N-substituted pyrrolidinyl).

The term "heterocyclic ring" refers to a heterocycloalkyl or heteroaryl ring system.

The term "heterocycloalkyl", as used herein includes non-aromatic ring systems having five to fourteen members, preferably five to ten, in which one or more ring carbons, preferably one to four, are each replaced by a heteroatom such as N, O, or S. Examples of heterocycloalkyl groups include 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl. Also included within the scope of the term "heterocycloalkyl", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycloalkyl", whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, 2-thienyl, 3-thienyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. Preferred heteroaryl groups are pyrrolyl, indolyl, pyridyl, pyridazinyl, pyrimidinyl, and pyrazinyl.

An arylalkyl group, as used herein, is an aryl substituent that is linked to a compound by an alkyl group having from one to five carbon atoms.

An alkoxy group, as used herein, is a C1-C5 alkyl group that is connected to a compound via an oxygen atom. Examples of alkoxy groups include but are not limited to methoxy, ethoxy, propoxy, isopropoxy, and t-butoxy.

A cycloalkoxy group, as used herein, is a cyclic C3-C12 hydrocarbon which is attached to a compound via an oxygen. Cycloalkoxy groups include but are not limited to cyclopropoxy and cyclobutoxy.

A hydroxyalkyl group, as used herein, is an alkyl group that is substituted with one or more hydroxy group. A preferred hydroxyalkyl is hydroxymethyl.

A haloalkoxy, as used herein, is a haloalkyl group that is attached to a compound via an oxygen. A preferred haloalkoxy is trifluoromethoxy.

An aryloxy, as used herein, is an aryl group that is attached to a compound via an oxygen. A preferred aryloxy is phenoxy.

A arylalkoxy group, as used herein, is a arylalkyl group that is attached to a compound via an oxygen on the C1-C5 alkyl portion of the arylalkyl. A preferred arylalkoxy is phenylmethoxy.

An alklythio group, as used herein, is a C1-C12 alkyl group that is connected to a compound via a sulfur atom.

An aryl (including aralkyl, aralkoxy, aryloxyalkyl and the like) or heteroaryl (including heteroaralkyl and heteroarylalkoxy and the like) may contain one or more substituents. Examples of suitable substituents include C1-C5 alkyl groups, aryl groups, haloalkoxy groups, heteroaryl groups, 1,2-methylene-dioxy, 1,2-ethylenedioxy, halo, hydroxy, $OR_{27}$, $COR_{27}$, $COOR_{27}$, $NHCOR_{27}$, $OCOR_{27}$, benzyl, haloalkyl (e.g., trifluoromethyl and trichloromethyl), halo, cyano, nitro, $SO^{3-}$, SH, $SR_{27}$, $NH_2$, $NHR_{27}$, $NR_{27}R_{28}$, and COOH, wherein $R_{27}$ and $R_{28}$ are each, independently, an aliphatic group, a cycloalkyl, an aryl group, or an arylalkyl group.

An alkyl group or a heterocycloalkyl may contain one or more substituents. Examples of suitable substituents on the saturated carbon of an alkyl group or a heterocycloalkyl include those listed above for an aryl or heteroaryl group and the following: =O, =S, =$NNHR_{31}$, =$NNR_{31}R_{32}$, =NNH-C(O)$R_{31}$, =NNHCO$_2$(alkyl), =NNHSO$_2$(alkyl), or =$NR_{31}$, wherein $R_{31}$ and $R_{32}$ are each, independently, selected from hydrogen or an unsubstituted alkyl. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, thioalkyl, nitro, cyano, carboxy, alkoxycarbonyl, alkylcarbonyl, hydroxy, haloalkoxy, or haloalkyl.

Suitable substituents on the nitrogen of a non-aromatic heterocycle or on an unsaturated nitrogen of a heteroaryl include —$R_{29}$, —$NR_{29}R_{30}$, —C(O)$R_{29}$, —CO$_2R_{29}$, —C(O)C(O)$R_{29}$, —C(O)CH$_2$C(O)$R_{29}$, —SO$_2R_{29}$, —SO$_2NR_{29}R_{30}$, —C(=S)$NR_{29}R_{30}$, —C(=NH)—$NR_{29}R_{30}$, and —$NR_{29}SO_2R_{30}$; wherein $R_{29}$ and $R_{30}$ are each, independently, hydrogen, a C1-C5 alkyl group, phenyl, substituted Ph, —O(Ph), —CH$_2$(Ph), or an unsubstituted heteroaryl or heterocycloalkyl. Examples of substituents on the aliphatic group or the phenyl ring include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

The term "pentose," as used herein, refers to a monosaccharide having five carbon atoms.

The term "hexose," as used herein, refers to a monosaccharide having six carbon atoms.

Compounds and pharmaceutical compositions of the invention that are represented by structural formulas A, I, II, III, IV, and V, and their pharmaceutically acceptable salts, are useful for the treatment of diseases or conditions in a mammal where increased activity of UCP2 contributes to the cause of the disease or condition. Examples of such diseases or conditions include deficient first-phase insulin secretion, non-insulin dependent diabetes mellitus, and ischemia.

Compounds represented by Structural Formula A are as provided in the Summary of the invention, with further definition as set forth below. In separate embodiments, each chemically possible combination of variables as defined herein is contemplated.

In independent embodiments, $X_4$ is —NR—, or —O—. Preferably, $X_4$ is —O—.

In some embodiments, $R_1$, taken together with a substituent of $X_3$ selected from $R_{10}$, $R_{11}$, $R_{12}$, $R_{13}$, $R_{14}$, and $R_{18}$, together with C7a, the carbon to which $R_1$ is attached, and the carbon represented by $X_3$, form a cyclic ether. Typically, $R_2$ is —OCH$_3$.

In various embodiments, $X_1$ is $CR_6R_7$, $X_2$ is $CR_8R_9$ and $X_3$ is $CR_{10}R_{11}$. Typically, the compound is selected from

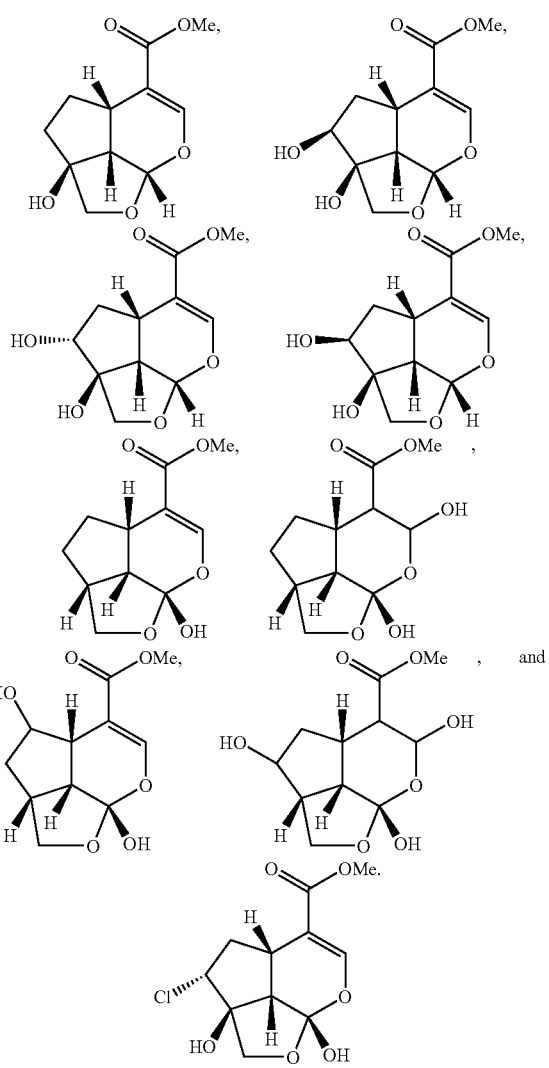

In other embodiments, the compound is selected from:

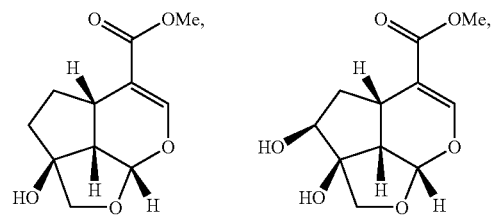

-continued

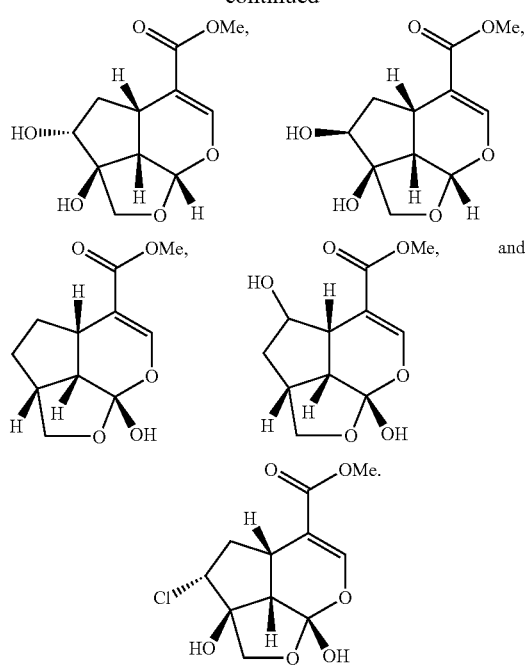

Preferably, the compound is:

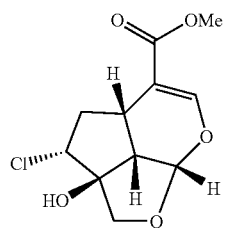

In other embodiments, $R_8$ and $R_{10}$ together with two adjacent carbons to which they are attached, form an epoxy ring; or $R_6$ and $R_8$ together with two adjacent carbons to which they are attached, form an epoxy ring. Typically, the compound is selected from

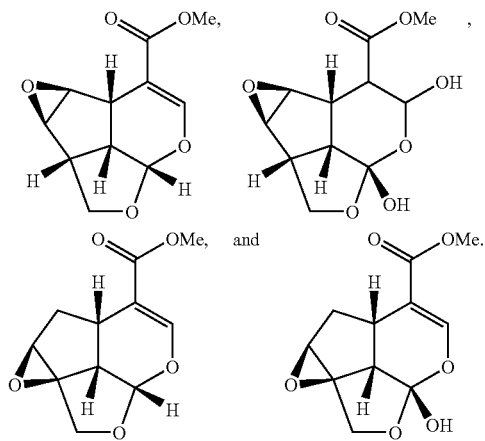

In other embodiments, the compound is selected from:

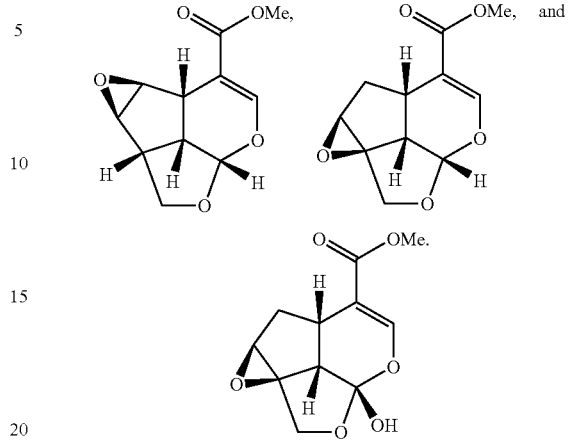

In still other embodiments, $X_1$ is $=CR_{18}-$, $X_2$ is $=CR_{12}-$, and $X_3$ is $CR_{13}R_{14}$. Typically, the compound is selected from

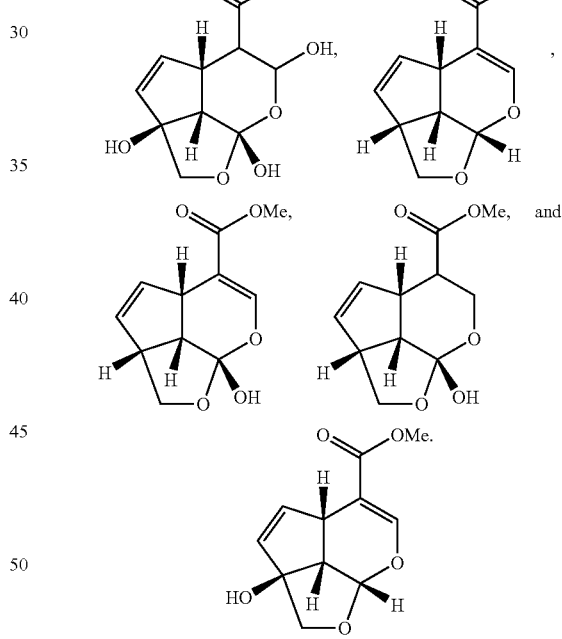

In other embodiments, the compound is selected from:

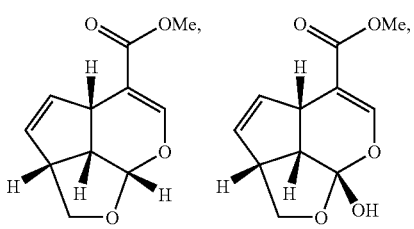

-continued

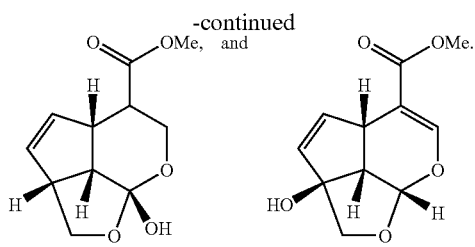

In yet other embodiments, $X_2$ is $=CR_{18}-$, $X_3$ is $=CR_{12}-$, and $X_1$ is $CR_{13}R_{14}$. Typically, the compound is selected from

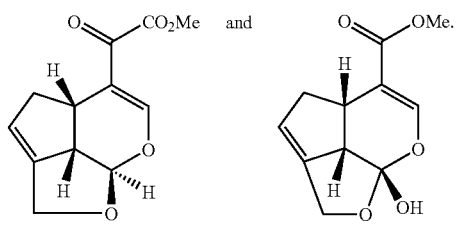

In various embodiments, $X_1$ is $CR_{13}R_{14}$, and $R_2$ and $R_{13}$, together with C4, C4a, the carbon to which $R_{13}$ is attached and the carbonyl group to which $R_2$ is attached, form a lactone ring. In some embodiments, $R_1$, taken together with a substituent of $X_3$ selected from $R_{10}$, $R_{11}$, $R_{12}$, $R_{13}$, $R_{14}$, and $R_{18}$, together with C7a, the carbon to which $R_1$ is attached, and the carbon represented by $X_3$, form a cyclic ether; typically, the compound is selected from

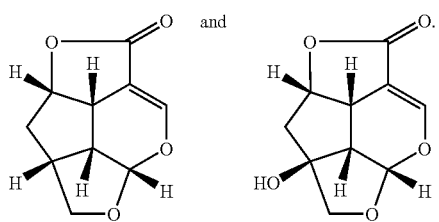

In other embodiments, $R_1$ is $—OH$, $=O$, $—OSi(R_{19})_3$, a hexose or pentose.

In one embodiment, the compounds of the invention are represented by structural formula VI, and pharmaceutically acceptable salts thereof:

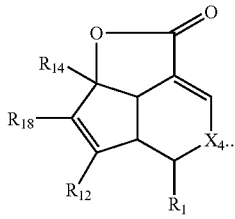

VI

In structural formula VI, $X_4$, $R_1$, $R_{12}$, $R_{14}$ and $R_{18}$ are defined as above.

In a second embodiment of the invention, $X_4$ is $—NR—$ in the compounds represented by structural formula I.

In a third embodiment of the invention, $X_4$ is $—O—$ in the compounds represented by structural formula I.

In a fourth embodiment of the invention, $X_4$ is $—NR—$ in the compounds represented by structural formula II, III, IV, V, or VI.

In a fifth embodiment of the invention, $X_4$ is $—O—$ in the compounds represented by structural formula II, III, IV, V, or VI.

In a sixth embodiment, $X_2$ is $=CR_{18}-$, $X_3$ is $=CR_{12}-$, and $X_1$ is $CR_{13}R_{14}$ in structural formula I, or in the second or third embodiment.

In a seventh embodiment, $X_1$ is $=CR_{18}-$, $X_2$ is $=CR_{12}-$, and $X_3$ is $CR_{13}R_{14}$ in structural formula I, or in the second or third embodiment.

In an eighth embodiment, $X_1$ is $CR_6R_7$, $X_2$ is $CR_8R_9$ and $X_3$ is $CR_{10}R_{11}$ in structural formula I, or in the second or third embodiment.

In another embodiment, $R_8$ and $R_{10}$ together with two adjacent carbons to which they are attached, form an epoxy ring in structural formula I, or in the second, third, or eighth embodiment.

In a tenth embodiment, $R_8$ and $R_{10}$ together with two adjacent carbons to which they are attached, form an epoxy ring, and $R_1$ is $—OH$, $R_2$ is $—OCH_3$, and $R_{11}$ is $—CH_2OH$. $—CH_2OC(O)NR_{15}R_{16}$ or $—CH_2OC(O)R_{17}$ in structural formula I, or in the second, third or eighth embodiment.

In an eleventh embodiment, $R_6$, $R_7$, and $R_8$ are H; $R_9$ and $R_{10}$ are $—OH$; and $R_{11}$ is $—CH_2OH$ in structural formula I, or in the second, third or eighth embodiment. More preferably, $R_1$ is $—OH$ or glucosyl and $R_2$ is $—OCH_3$ in this embodiment.

In a twelfth embodiment, $R_6$, $R_7$, $R_8$ and $R_{10}$ are H; $R_9$ is $—OH$; and $R_{11}$ is $—CH_3$ in structural formula I, or in the second, third or eighth embodiment. More preferably, $R_1$ is $—OH$ or glucosyl and $R_2$ is $—OCH_3$ in this embodiment.

In a thirteenth embodiment, $R_6$, $R_8$ and $R_9$ are H; $R_7$ and $R_{10}$ $—OH$; and $R_{11}$ is $—CH_3$ in structural formula I, or in the second, third or eighth embodiment. More preferably, $R_1$ is $—OH$ or glucosyl and $R_2$ is $—OCH_3$.

In a fourteenth embodiment, $R_1$ is $=O$ in structural formula I, II, III, IV, V, VI or in the any one of the above embodiments.

In a fifteenth embodiment, $R_{12}$ is $—CH_2OH$ and $R_2$ is $—OCH_3$ in structural formula I, II, III, IV, V, VI or in the any one of the above embodiments.

In a sixteenth embodiment, $X_4$ is $—O—$; $X_2$ is $=CR_{18}-$; $X_3$ is $=CR_{12}-$; and $X_1$ is $CR_{13}R_{14}$ in structural formula I. Preferably, $R_1$ is $=O$, $—OH$, or glucosyl in this embodiment. More preferably, $R_1$ is $=O$, $—OH$, or glucosyl; and $R_{12}$ is $—CH_3$ or $—CH_2OH$ in this embodiment.

In a seventeenth embodiment, $R_{20}$ is $—OCH_3$; and $R_1$ is $—OH$ or glucosyl in structural formula II. More preferably, Ring A is substituted with p-hydroxy and m-hydroxy.

In an eighteenth embodiment, $X_4$ is $—O—$; and $R_1$ is $—OH$ or glucosyl in structural formula III.

First-phase insulin secretion refers to an initial sharp rise in insulin in response to elevated blood glucose levels. A glucose tolerance test may be used to evaluate whether a mammal's first-phase insulin secretion is deficient. In one example of a glucose tolerance test, a mammal is administered an injection of glucose, typically 0.3 g/kg of body weight, and insulin levels in the mammal's blood are measured periodically, for example every 30 sec. First-phase insulin secretion is a result of the release of stored granules and, typically, reaches a maximum at about 3 min. to about 5 min. Generally, first-phase insulin secretion lasts about 10 min. and a maximum plasma insulin level of about 100 µU/mL or more is reached. Deficient first-phase insulin response is a maximum plasma insulin level in response to a glucose tolerance test of less than about 100 µU/mL. More preferably, deficient first-phase insulin response is a maximum plasma insulin level in response to a glucose tolerance test of less than about 50 µU/mL.

Oxidative metabolism of glucose is shown schematically in FIG. 1. Mitochondrial oxidation of glucose generates NADH and $FADH_2$ which donate electrons to the mitochondrial inner membrane electron transport chain. As electrons move down this chain, protons are pumped out of the mitochondrial matrix by complexes I (NADH-ubiquinone oxidoreductase), III (ubiquinone-cytochrome-c oxidoreductase) and IV (cytochrome oxidase), creating a proton electrochemical gradient. Molecular oxygen ($O_2$) is the terminal electron acceptor. Protons are pumped out by complexes I, III and IV of the electron transport chain creating a proton electrochemical gradient ($\Delta\mu_{H+}$). Protons may reenter the mitochondrial matrix via ATP synthase ($F_0F_1$), with energy being used to generate ATP from ADP and Pi. This proton motive force is then used by ATP synthase to generate ATP from ADP (Scheffler, I. E., *Mitochondria* (Wiley-Liss, New York, 1999) pp. 141-245.)

Pancreatic β cells sense glucose through its metabolic product, ATP. As described above, glucose metabolism results in an increased ATP/ADP ratio which causes ATP-sensitive potassium ion channels ($K_{ATP}$ channels) to close resulting in plasma membrane depolarization. Plasma membrane depolarization causes an influx of $Ca^{2+}$ which results in insulin secretion.

Uncoupling protein 2 (UCP2) (Fleury, C., et al., *Nat. Genet*, 15:269 (1997); Gimeno, R. E., et al., *Diabetes*, 46:900 (1997)) and uncoupling protein 3 (UCP3) (Boss, O., et al., *FEBS Lett.*, 408:39 (1997); Vidal-Puig, A., et al., *Biochem. Biophys. Res. Commun.*, 235:79 (1997); Gong, D. W., et al., *J. Biol. Chem.* 272:24129 (1997)) are recently discovered members of the mitochondrial inner membrane carrier family with high homology to UCP1 (Nicholls, D. G., et al., *Physiol. Rev.*, 64:1 (1984); Klingenberg, M., and Huang, S. G., *Biochim. Biophys. Acta.*, 1415:271 (1999)) and expression patterns which are consistent with the hypothesis that they play a role in the regulation of cellular processes in which ATP plays a regulatory function. UCP3 is expressed primarily in skeletal muscle where it likely plays a role in regulated thermogenesis. In contrast, UCP2 has a nearly ubiquitous expression pattern, but at varying levels in a number of tissues and cell types including tissues involved in glucose homeostasis (pancreatic islets, white fat, brown fat, heart, skeletal muscle). For example, UCP2 mRNA (Zhou, Y. T., et al., *Proc. Natl. Acad. Sci. U.S.A.,* 94:6386 (1997); Chan, C. B., et al., *Diabetes* 48:1482 (1999)) and protein are highly expressed in pancreatic β-cells.

Studies in which UCP2 and UCP3 have been overexpressed in yeast (Rial, E., et al., *EMBO J.,* 18:5827 (1999); Hinz, W., et al., *FEBS Lett,* 448:57 (1999); C. Y. Zhang, et al., *FEBS Lett,* 449:129 (1999)) or reconstituted into proteoliposomes (Jaburek, M., et al., *J. Biol. Chem.,* 274:26003 (1999)) indicate a proton leak (and as a consequence modulator of ATP) role for these new UCPs. The present inventors have developed a transgenic UCP2 knockout mouse (U.S. Pat. No. 6,365,796, the entire teachings of which are incorporated herein by reference) that definitively shows that a function of UCP2 is to leak protons into the mitochondrial matrix which dissipates protomotive force as heat and results in a decrease in ATP/ADP ratio. In pancreatic β cells, this decreased ATP/ADP ratio results in a decrease in insulin secretion.

β-cell function deteriorates in many individuals with obesity and insulin resistance, culminating in the development of type II diabetes mellitus. UCP2 is markedly upregulated in β cell islets of ob/ob obese mice, a model of obesity-induced diabetes indicating that obesity-induced UCP2 expression in β-cells contributes to β-cell dysfunction, promoting the development of diabetes. Consistent with this theory, it has been reported that UCP2 lies within a major quantitative trait loci (QTL) (murine chromosome 7; rat chromosome 1 and human chromosome 11) controlling diet-induced hyperinsulinemia in C57Bl/6 mice (Fleury, C., et al., *Nat. Genet,* 15:269 (1997); Seldin, M. F., et al., *J. Clin. Invest.,* 94:269 (1994)); glucose intolerance and adiposity in the GK (Goto-Kakizaki) model of type 2 diabetes the rat (Gauguier, D., et al., *Nat. genet.,* 12:38 (1996); Galli, J., et al., *Nat. genet.,* 12:31 (1996); Kaisaki, P. J., et al., *Mamm. genome,* 9:910 (1998)), and human insulin-dependent diabetes locus-4 (Fleury, C., et al., *Nat. Genet.,* 15(3):269-272 (1997)).

It has been shown that addition of high levels of superoxide to isolated mitochondrial stimulates proton leak if UCP1, UCP2 or UCP3 (collectively "UCPs") are present. To determine whether endogenous levels of superoxide could also stimulate the activity of UCPs, the present inventors have shown that addition of a superoxide dismutase mimetic, MnTBAP, which reduces superoxide, to isolated thymocytes decreases proton leak. However, this effect is not present in thymocytes that are deficient in UCP2 indicating that endogenous levels of superoxide in intact cells tonically activates proton leak mediated by UCP2. In addition, treating isolated islets with MnTBAP increased ATP levels and increased insulin secretion. This effect was also absent in UCP2 deficient islets indicating not only that decreasing the levels of superoxide decreases proton leak mediated by UCP2, but also that decreased UCP2 activity increases ATP production and insulin secretion.

Understanding of this previously unknown pathway which regulates insulin secretion has resulted in the development of compounds of the invention that are useful in the treatment of diseases or conditions, such as Type II diabetes, where increased activity of UCP2 contributes to the cause of the disease or condition. In one embodiment, the compounds of the invention are useful in treating the early stages of Type II diabetes. An individual in the early stages of Type II diabetes may be able to control their blood sugar through diet alone or may take medications such as sulfonylureas, thiazolidinediones or metformin to control their blood sugar but may not require insulin injections. As the disease progresses, a person in the early stages of diabetes may require insulin injections to control their blood sugar but may not exhibit complications of the disease such as cataracts, retinopathy, nephropathy, and the like.

In addition, the compounds of the invention are useful in treating ischemia reperfusion damage. Reactive oxygen species, such as superoxide, are believed to accumulate when tissues are subjected to ischemia followed by reperfusion, such as occurs following a stroke or myocardial infarction. Increased superoxide levels increases the activity of UCP2 which is believed to contributes to tissue damage after ischemia reperfusion. The compounds of the invention are useful in treating ischemia reperfusion injuries, such as stroke and myocardial infarction, because they inhibit the activity of UCP2.

The language a "therapeutically effective amount" or "pharmaceutically effective amount" is intended to include an amount which is sufficient to mediate a disease or condition and prevent its further progression or ameliorate the symptoms associated with the disease or condition. Such an amount can be administered prophylactically to a patient thought to be susceptible to development of a disease or condition. For example, indications that a person is susceptible to diabetes mellitus include obesity and deficient first-phase insulin secretion. Such amount when administered prophylactically to a patient can also be effective to prevent or lessen the severity of the mediated condition. Such an amount is intended to include an amount which is sufficient to inhibit UCP2, which mediate a disease or condition. Conditions mediated by UCP2 include, for example, diabetes mellitus and ischemia.

The compounds of structural formulas I, II, III, IV, V and VI and the pharmaceutically acceptable salts thereof, have valuable pharmacological properties and can be used in pharmaceutical preparations containing one or more compound or pharmaceutically acceptable salts thereof, in combination with a pharmaceutically acceptable carrier or diluent. They are useful as therapeutic substances in preventing or treating conditions such as diabetes mellitus and/or ischemia reperfusion disease in human or non-human animals. Suitable pharmaceutically acceptable carriers include inert solid fillers or diluents and sterile aqueous or organic solutions. The active compound will be present in such pharmaceutical compositions in amounts sufficient to provide the desired dosage amount in the range described herein. Techniques for formulation and administration of the compounds of the instant invention can be found in Remington: the Science and Practice of Pharmacy, 19th edition, Mack Publishing Co., Easton, Pa. (1995).

For oral administration, the compound or salts thereof can be combined with a suitable solid or liquid carrier or diluent to form capsules, tablets, pills, powders, syrups, solutions, suspensions and the like.

The tablets, pills, capsules, and the like may also contain a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The active compounds can also be administered intranasally as, for example, liquid drops or spray. For oral or nasal inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

For parenteral administration the compounds of the present invention, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, ethanol, polyol (e.g. glycerol, propylene glycol and liquid polyethylene glycol), propylene glycol and liquid polyethylene glycol), suitable mixtures thereof, and vegetable oils. The injectable solutions prepared in this manner can then be administered intravenously, intraperitoneally, subcutaneously, or intramuscularly, with intramuscular administration being preferred in humans.

The compounds may also be formulated in rectal compositions such as suppositories or retention enemas, e.g., containing conventional suppository bases such as cocoa butter or other glycerides.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

The effective dosage of active ingredient employed may vary depending on the particular compound employed, the mode of administration, the condition being treated and the severity of the condition being treated.

The compositions are formulated and administered in the same general manner as detailed herein. Compounds of the instant invention may be used effectively alone or in combination with one or more additional active agents depending on the desired target therapy. Combination therapy includes administration of a single pharmaceutical dosage formulation which contains a compound of structural formula I, II, III, IV, V or VI and one or more additional active agents, as well as administration of a compound of structural formula I, II, III, IV, V or VI and each active agent in its own separate pharmaceutical dosage formulation. For example, a compound of structural formula I, II, III, IV, V or VI or a pharmaceutically acceptable salt thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of structural formula I, II, III, IV, V or VI and one or more additional active agents can be administered at essentially the same time, i.e., concurrently, or at separately staggered times, i.e., sequentially; combination therapy is understood to include all these regimens.

Another example of combination therapy can be seen in treating diabetes and related disorders wherein the compounds of structural formula I, II, III, IV, V or VI, or salts thereof can be effectively used in combination with, for example, sulfonylureas, biguanides, thiazolidinediones, α-glucosidase inhibitors, other insulin secretogogues, and insulin.

A therapeutically effective amount of a compound of structural formula I, II, III, IV, V or VI can be used for the preparation of a medicament useful for treating diabetes. In general, a therapeutically effective amount of a compound of Structural Formula I, II, III, IV, V or VI reduces serum glucose levels of a patient, or more specifically HbA1c, typically by about 0.7%.

Preferably compounds of the invention or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Structural Formula I or salts thereof) in a unit dose of composition is a therapeutically effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Pharmaceutical formulations of the invention are prepared by combining (e.g., mixing) a therapeutically effective amount of a compound of the invention together with a pharmaceutically acceptable carrier or diluent. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of about 0.05 to about 5.0 mg/mL in a 4% dextrose/0.5% Na citrate aqueous solution.

Solid form formulations include powders, tablets and capsules. A solid carrier can be one or more substance which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired.

Advantageously, compositions containing the compound of structural formula I, II, III, IV, V or VI or salts thereof may be provided in dosage unit form, preferably each dosage unit containing from about 1 to about 500 mg be administered although it will, of course, readily be understood that the amount of the compound or compounds of structural formula I, II, III, IV, V or VI actually to be administered will be determined by a physician, in the light of all the relevant circumstances.

Powders and tablets preferably contain from about 1 to about 99 weight percent of the active ingredient which is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

The following pharmaceutical formulations 1 through 8 are illustrative only and are not intended to limit the scope of the invention in any way. "Active Ingredient", refers to a compound according to structural formula I, II, III, IV, V or VI or salts thereof.

Formulation 1

Hard gelatin capsules are prepared using the following ingredients:

|  | Quantity (mg/capsule) |
|---|---|
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight (mg) |
| --- | --- |
| Active Ingredient | 0.25 |
| Ethanol | 25.75 |
| Propellant 22 (Chlorodifluoromethane) | 74.00 |
| Total | 100.00 |

The Active Ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

|  | Quantity(mg/tablet) |
| --- | --- |
| Active Ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active Ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active Ingredient, are made as follows:

|  | Quantity(mg/tablet) |
| --- | --- |
| Active Ingredient | 80 mg |
| Starch | 59 mg |
| Microcrystalline cellulose | 59 mg |
| Magnesium stearate | 2 mg |
| Total | 200 mg |

The Active Ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active Ingredient, are made as follows:

|  | Weight |
| --- | --- |
| Active Ingredient | 225 mg |
| Saturated fatty acid glycerides | 2,000 mg |
| Total | 2,225 mg |

The Active Ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active Ingredient per 5 mL dose, are made as follows:

|  | amount |
| --- | --- |
| Active Ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v |
| Purified water to total | 5 mL |

The Active Ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

|  | amount |
| --- | --- |
| Active Ingredient | 100 mg |
| Isotonic saline | 1,000 mL |

The solution of the above materials generally is administered intravenously to a subject at a rate of 1 mL per minute.

Synthesis

A number of iridoids related to genipin are candidate inhibitors of UCP-2. Chemical syntheses of target inhibitors derived from genipin are shown in Schemes I through IV. The synthesis of gardenamide A (2), a natural product prepared from genipin (1) is shown in Scheme I (see Bringmann, et al., *Eur. J. Org. Chem.* 2001, 1983-1987, the entire teachings of which have been incorporated herein by reference). The nitrogen of the ring amide may be substituted with a variety of alkyl, aralkyl or heteroaralkyl groups by using a primary amine in step 3 of the synthesis that is substituted with an alkyl, aralkyl or heteroaralkyl group. Alternatively, gardenamide with an unsubstituted amide nitrogen can be prepared by using ammonium hydroxide in step 3. In addition, the methyl ester group of gardenamide may be converted to a carboxylic acid, amide or a different ester by methods known to those skilled in the art.

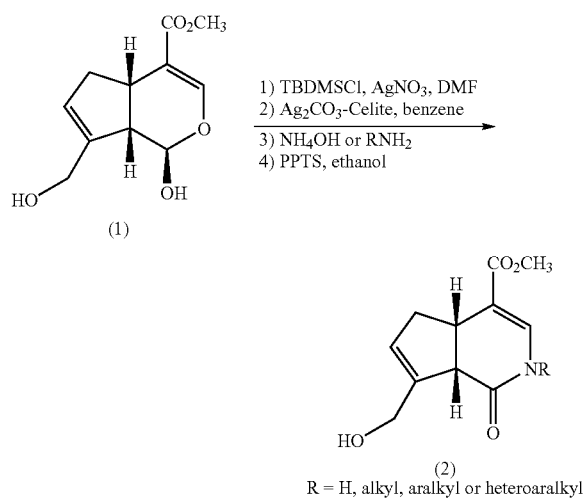

Scheme II shows a method of preparing genipin analogue (5) from genipin (1) by protecting the free alcohol groups with a silyl protecting group such as t-butyldiphenylsilyl (TBDPS) or t-butyldimethylsilyl (TBDMS). Epoxidation of silyl intermediate is then effected by treatment with m-chloroperbenzoic acid (MCPBA) to form intermediate (4). The silyl protecting group is then removed from intermediate (4) by treatment with tetrabutylammonium fluoride (TBAF) to form genipin analogue (5).

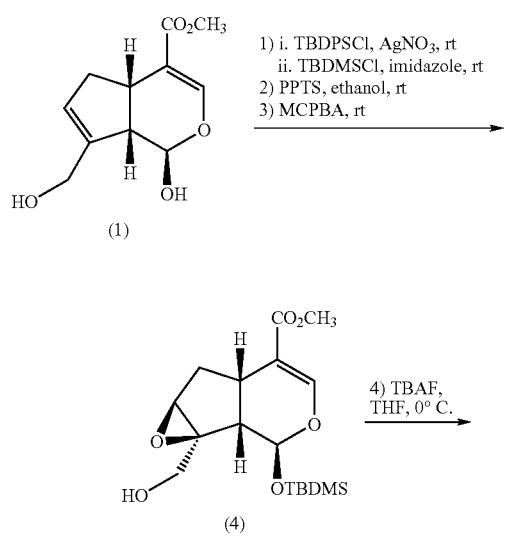

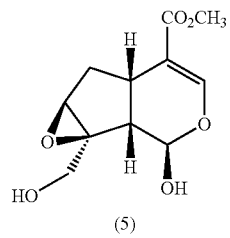

Hydrogenation of the allylic double bond of geniposide (6), as shown in Scheme III, may be effected by hydrogen (in the presence of a catalyst such as platinum on carbon) (see Mansour, et al., *Curr. Pharm. Design* 1997, 3:227-264, the entire teachings of which are incorporated herein by reference), followed by hydrolysis of the carbohydrate moiety with β-glucosidase to form genipin derivatives (7) and (8) (see Miyagoshi, et al., *Planta Medica* 1987, 53:462-464 and Fujikawa, et al., *J. Biotechnology Letters* 1987, 9:697-702, both of which are incorporated herein by reference in their entirety).

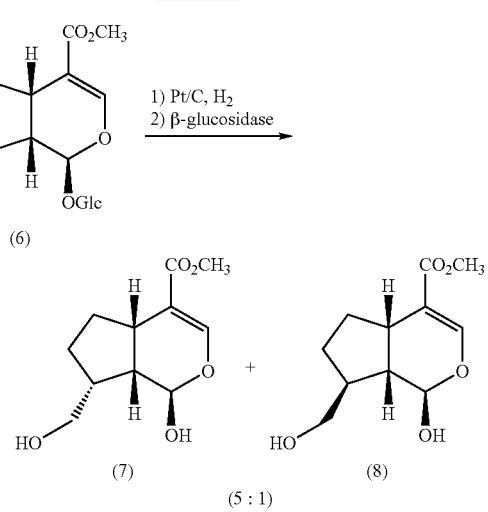

The dihydroxylated genipin derivative (9), shown in Scheme IV, can be formed by bis-silylation of genipin (1) with a silyl protecting group such as TBDMS, followed by stereoselective osmylation using osmium tetroxide to form a diol which is subsequent deprotection with TBAF to form genipin derivative (9) (see Nakatani, et al., *Bull. Chem. Soc. Japan* 1993, 66:2646-2652, the entire teachings of which are incorporated herein by reference).

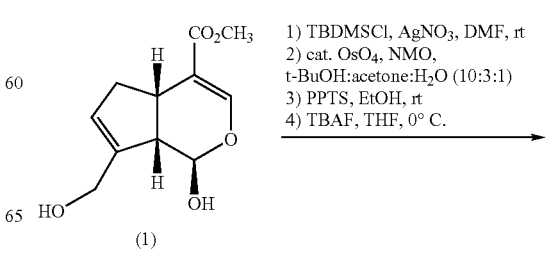

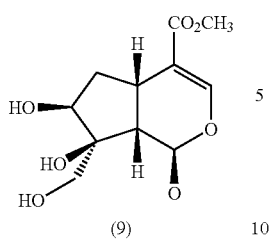

(9)

Additional functional group transformations can be introduced onto molecules such as those prepared in Schemes I through IV to prepare candidate UCP-2 inhibitors. For example, intermediate (4) can be reacted with a isocyanate to prepare a carbamate. The TBDMS protected lactol is then deprotected with TBAF to form genipin derivative (10) (see Scheme V).

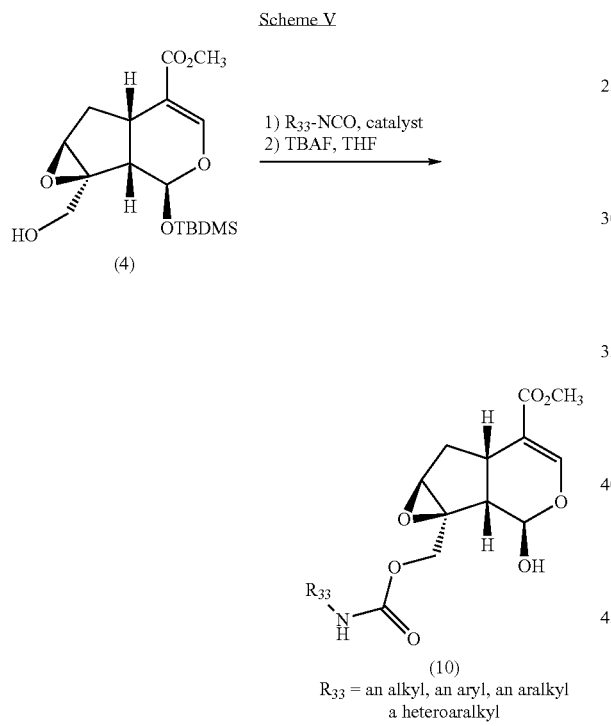

In addition, the primary alcohol group of intermediate (4) may be esterified via carbodiimide coupling or other esterification methods to form esters such as (11) (see Scheme VI).

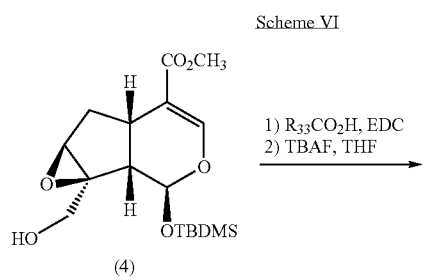

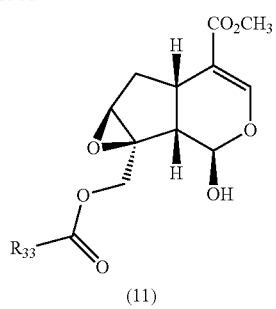

(11)

The alcohol groups of genipin may be protected with, for example, TBDMS to form intermediate (12), as shown in Scheme VII. The methyl ester functionality of intermediate (12) may then be transformed into the amide (13) via hydrolysis of intermediate (12) with lithium hydroxide, followed by coupling of various amines using, for example, 1-(3-dimethylaminopropyl)-3-ethylcarbodiimmide hydrochloride (EDC) and 1-hydroxybenzotriazole hydrate (HOBT). Other genipin derivatives having structures similar to intermediate (13) may be modified in a likewise manner provided that the corresponding primary alcohol or methyl ester is present.

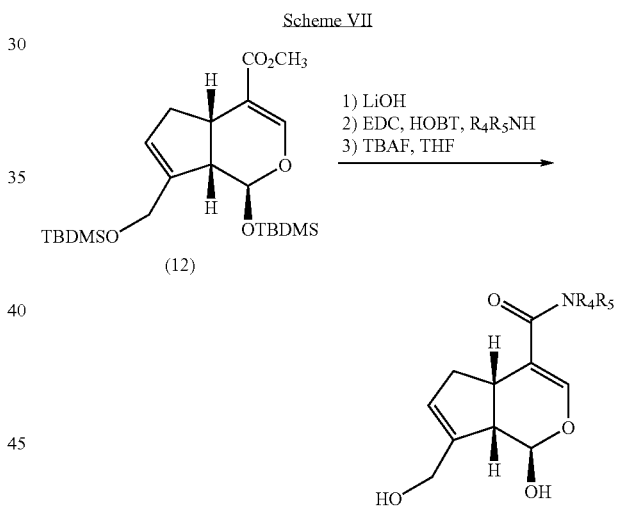

The iridoid compounds shown in Scheme VIII are UCP2 inhibitors. Iridoid glucosides can be converted to the respective iridoid aglycons by treatment with β-glucosidase. Iridoid glucosides shown in Scheme VIII are commercially available and may be used to prepare iridoid aglycons as candidate UCP-2 inhibitors. For example, iridoids bearing a methyl ester such as the glucosides verbenalin (14), loganin (16), geniposide (18), oleuropein (20), and gardenoside 22 which may be converted into their respective aglycons (15, 17, 19, 21, 23). The other two common forms of iridoids are carboxylic acid derivatives such as loganic acid (24), geniposidic acid (26), shanzhiside (28), and scandoside (30) which may be hydrolyzed to candidate aglycone inhibitors (25), (27), (29), and (31). Likewise, iridoid glucoside lactones such as asperuloside (32), deoxyasperuloside (33), and sweroside (35) may be transformed into potential UCP-2 inhibitors (34-36).

Scheme VIII

Methyl Esters

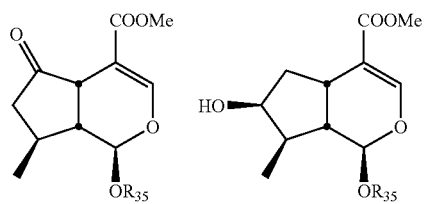

verbenalin
14 $R_{35}$ = glucose
15 $R_{35}$ = H loganin
16 $R_{35}$ = glucose
17 $R_{35}$ = H

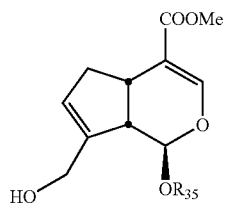

geniposide
18 $R_{35}$ = glucose
19 $R_{35}$ = H

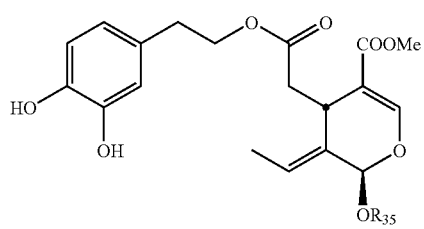

oleuropein
20 $R_{35}$ = glucose
21 $R_{35}$ = H

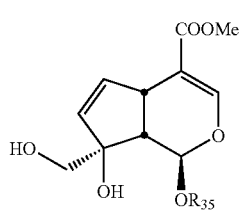

gardenoside
22 $R_{35}$ = glucose
23 $R_{35}$ = H

Acids

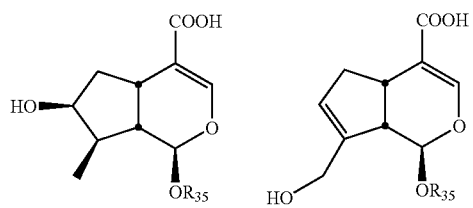

loganic acid
24 $R_{35}$ = glucose
25 $R_{35}$ = H geniposidic acid
26 $R_{35}$ = glucose
27 $R_{35}$ = H -continued

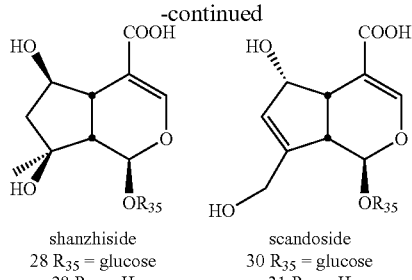

shanzhiside
28 $R_{35}$ = glucose
28 $R_{35}$ = H scandoside
30 $R_{35}$ = glucose
31 $R_{35}$ = H Lactones

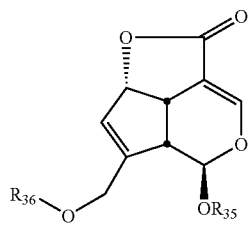

asperuloside
32 $R_{35}$ = glucose, $R_{36}$ = $COCH_3$
deacetylasperuloside 33 $R_{35}$ = glucose, $R_{36}$ = H
34 $R_{35}$ = H, $R_{36}$ = $COCH_3$. 35 $R_{35}$ = H, $R_{36}$ = H.

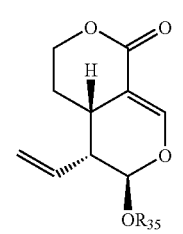

sweroside 35 $R_{35}$ = glucose
36 $R_{35}$ = H

Preparation of Genipin Derivatives and Evaluation of Bioactivities

Scheme IX. First Genipin Derivatives.

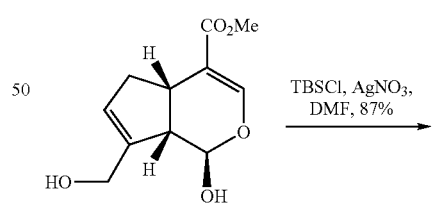

41

$\xrightarrow{\text{TBSCl, AgNO}_3,\text{ DMF, 87\%}}$

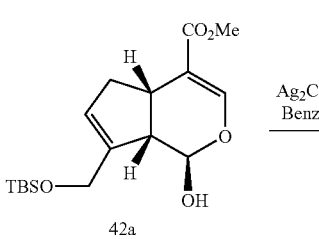

42a $\xrightarrow{\text{Ag}_2\text{CO}_3\text{-Celite, Benzene, 56\%}}$

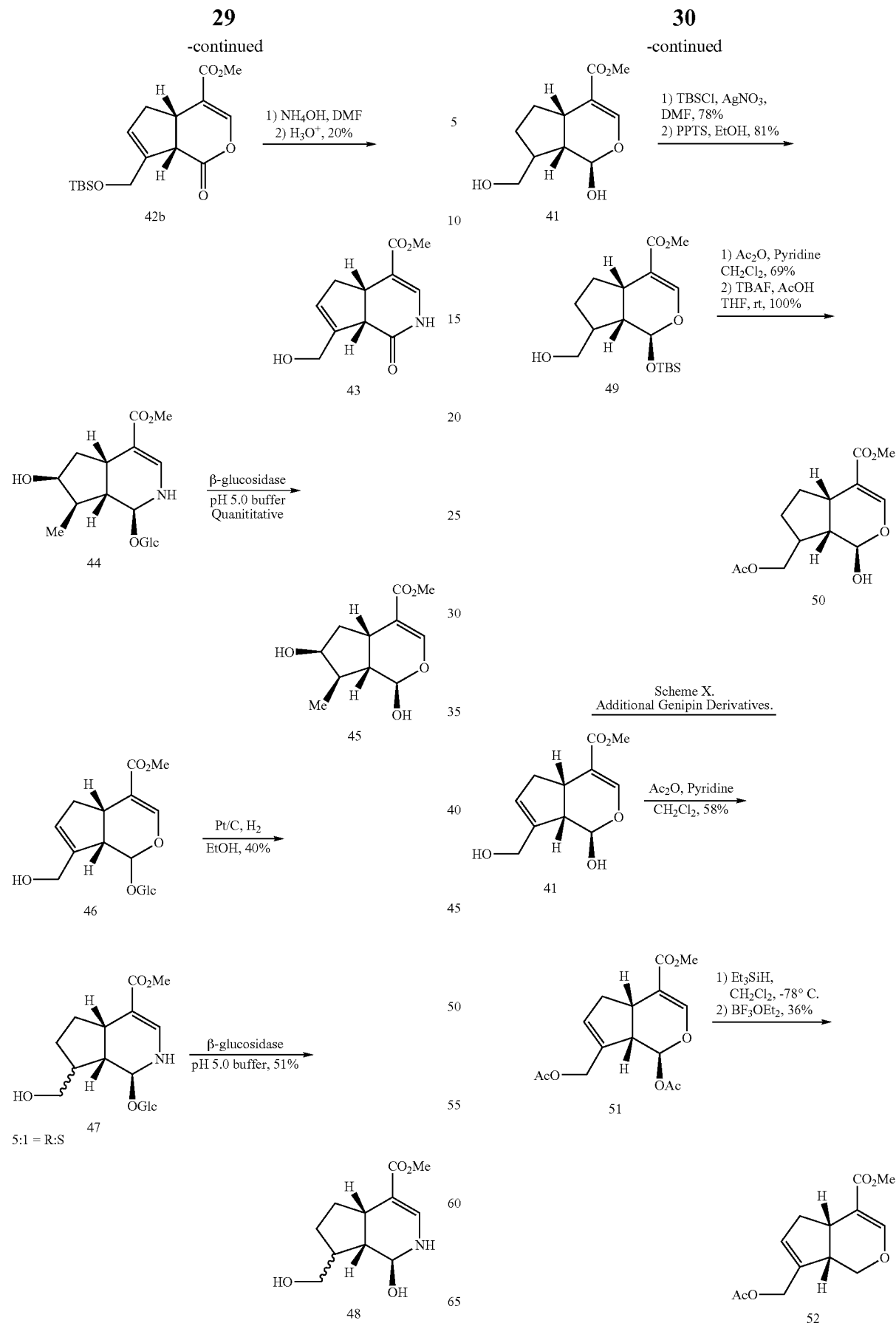

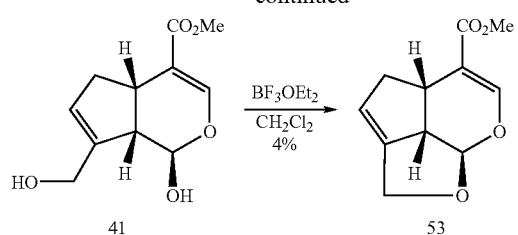

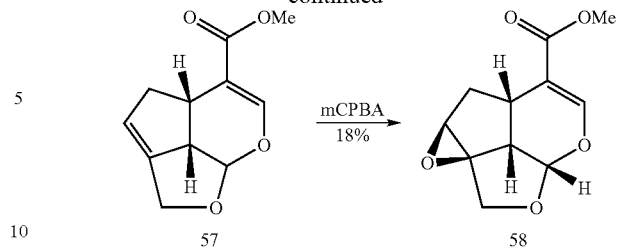

Scheme XI.
Synthesis of Tricyclic Genipinoid Derivatives.

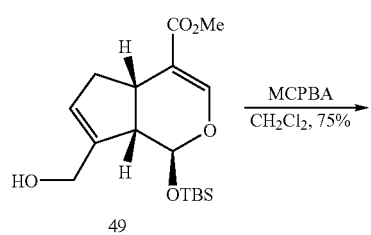

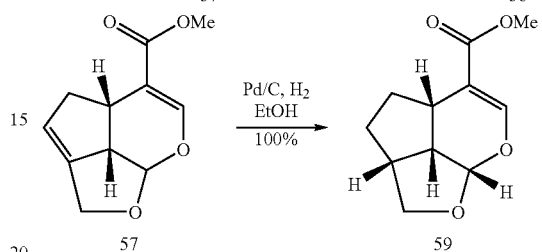

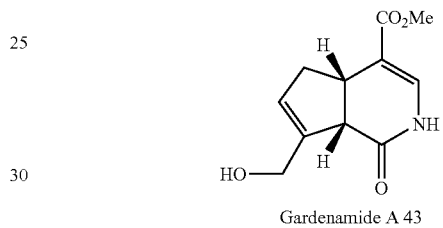

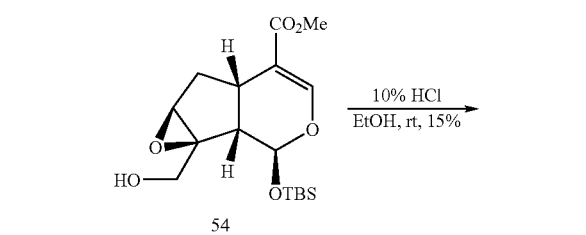

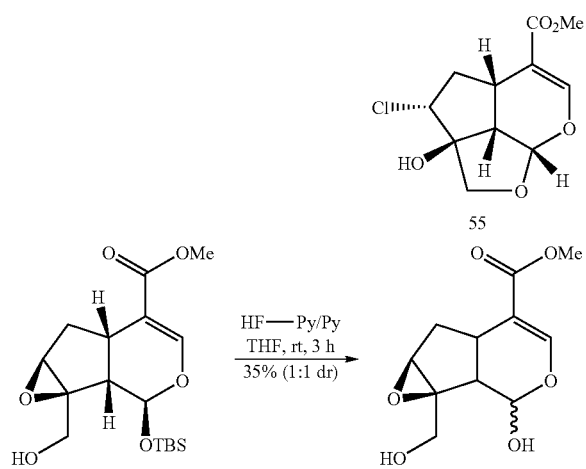

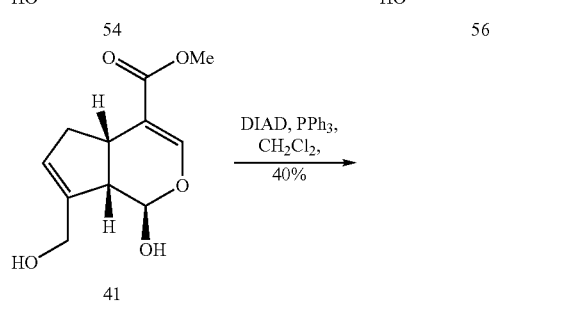

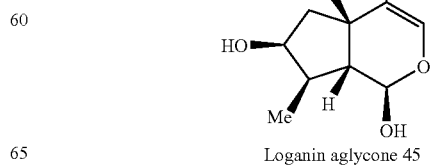

Fetizon's reagent was freshly prepared from $AgNO_3$ (1.5 g, 8.82 mmol), Celite (1.3 g), and $Na_2CO_3$ (700 mg, 6.62 mmol). Compound 42a (100 mg, 0.294 mmol) was dissolved in 18.5 mL Benzene. Dried fetizon's reagent (2.5 g, 4.41 mmol) was added to the solution and the reaction mixture was refluxed at 80° C. for 15 h. After cooling the mixture to room temperature, the solution was filtered through a pad of silica gel and the pad washed further with EtOAc. The filtrate was combined and concentrated in vacuo, and purification on silica gel (hexane:EtOAc=4:1) to afford 56 mg (56%) of lactone 42b. Then, 42b (15 mg, 0.044 mmol) was dissolved in 1 mL DMF and aq. $NH_4OH$ (12.5 mL, 0.22 mmol) was added to the solution. The reaction mixture was stirred for 10 min, quenched with 1M HCl (300 μL, 0.3 mmol), and extracted with EtOAc (3×). The organic layers were combined, dried over $Na_2SO_4$, and concentrated in vacuo. Purification by preparative HPLC (Symmetry® C18 5 μm, 10-100% $CH_3CN$/$H_2O$ 0-10 min) provides 2 mg (20%) of gardenamide A 43 (Rt=5.09 min). $^1H$ NMR (300 MHz, $CDCl_3$) δ 7.39 (1H, br s), 7.17 (1H, d, J=7.2 Hz), 5.84 (1H, s), 4.32 (2H, m), 3.74 (3H, s), 3.62 (1H, d, J=14.4 Hz), 2.91 (1H, J=16.5, 7.2 Hz), 2.23 (1H, dd, J=16.5, 8.7 Hz).

Loganin 44 (50 mg, 0.128 mmol) was dissolved in 1 mL 0.1M pH=5 buffer. To the solution was added 20 mg β-glucosidase (crude from almond). The reaction mixture was stirred at rt for 1 h and quenched with aqueous saturated sodium bicarbonate. The aqueous layer was extracted with EtOAc (3×), dried over Na$_2$SO$_4$, and concentrated in vacuo. Purification on silica gel (hexane:EtOAc=1:1) provided 29 mg (99%) of 45 as a colorless oil. $^1$H NMR (400 MHz, CDCl$_3$): δ 7.39 (1H, s), 4.97 (1H, dd, J=5.6, 5.6 Hz), 4.12 (1H, m), 3.69 (3H, s), 3.29 (1H, d, J=6.0 Hz), 3.17 (1H, m), 2.30 (1H, dd, J=7.6, 14.0 Hz), 1.96 (1H, m), 1.88 (1H, m), 1.56 (1H, m), 1.12 (3H, d, J=6.8 Hz); $^{13}$C NMR (300 MHz, CDCl$_3$): δ 168.3, 151.6, 111.6, 95.6, 74.3, 51.2, 46.2, 42.0, 41.3, 31.3, 13.1.

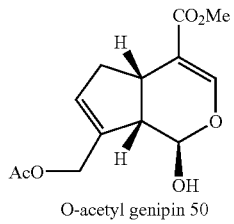

O-acetyl genipin 50

Compound 49 (40 mg, 0.118 mmol) was dissolved in 600 µL CH$_2$Cl$_2$, then Ac$_2$O (12.2 µL, 0.129 mmol) and Pyridine (14.2 µL, 0.176 mmol) were added. The reaction mixture was stirred at room temperature overnight. The reaction was quenched with H$_2$O. The aqueous layer was extracted with EtOAc (3×), dried over Na$_2$SO$_4$ filtered, and concentrated in vacuo. Purification through a silica gel column (hexane:EtOAc=4:1) yields 31 mg (69%) of a liquid, which was then used for the next reaction. The liquid (17 mg, 0.044 mmol) was dissolved in 600 µL THF. To the reaction mixture was added AcOH (2.8 mL, 0.0488) and 1.0M TBAF in THF (48.8 µL, 0.0488 mmol). The reaction was stirred at room temperature for 4 h. TBAF was quenched with H$_2$O and the aqueous extracted with EtOAc (3×). The organic layers were combined, dried over Na$_2$SO$_4$, and concentrated in vacuo. Column purification with silica gel (hexane/EtOAc) provided 14 mg (100%) of 50 as a yellowish liquid. $^1$H NMR (300 MHz, CDCl$_3$) δ 7.50 (1H, s), 5.93 (1H, s), 4.95 (1H, d, J=13.2 Hz), 4.76 (1H, d, J=8.4 Hz), 4.65 (1H, d, J=13.2 Hz), 4.59 (1H, s), 3.70 (3H, s), 3.18 (1H, ddd, J=8.7, 8.4, 8.4 Hz), 2.88 (1H, dd, J=16.8, 9.6 Hz), 2.49 (1H, dd, J=7.8, 7.8 Hz), 2.09 (3H, s), 2.03 (1H, m).

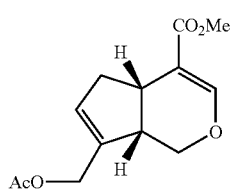

Dihydro pyran 52

Compound 51 (34 mg, 0.111 mmol) was dissolved in 1.11 mL of CH$_2$Cl$_2$ and the reaction mixture was cooled to −78° C. Triethylsilane (92 µL, 1.11 mmol) was added, followed by BF$_3$.OEt$_2$ (141 µL, 1.11 mmol). The mixture was stirred from −78° C. to room temperature overnight, then quenched with saturated sodium bicarbonate. The aqueous layer was extracted with EtOAc (3×). The organic layers were combined, washed with brine, dried over Na$_2$SO$_4$, and concentrated in vacuo. Purification by silica gel chromatography (hexane:EtOAc=6:1) afford 10 mg (36%) of 52 as a yellowish solid. $^1$H NMR (400 MHz, CDCl$_3$) δ 7.65 (1H, s), 5.86 (1H, s), 4.68 (1H, d, J=13.2 Hz), 4.57 (1H, d, J=13.2 Hz), 4.29 (1H, dd, J=11.2, 4.8 Hz), 3.70 (3H, s), 3.40 (1H, dd, J=10.0, 10.0 Hz), 3.06 (1H, ddd, J=8.4, 8.4, 8.4 Hz), 2.87 (1H, dd, J=18.0, 11.2 Hz), 2.68 (1H, m), 2.06 (3H, s), 2.06 (1H, m).

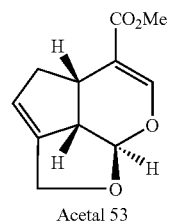

Acetal 53

Genipin 41 (50 mg, 0.221 mmol) was dissolved in 5 mL CH$_2$Cl$_2$. The solution was cooled to −78° C. Then, BF$_3$.OEt$_2$ (56 µL, 0.442 mmol) was dissolved in 5 mL CH$_2$Cl$_2$ and added to the reaction mixture. The solution was stirred from −78° C. to room temperature overnight. The reaction was quenched with saturated sodium bicarbonate, extracted with EtOAc (3×). Brine was added and the aqueous layer was further extracted with EtOAc (3×). The organic layers were combined, dried over Na$_2$SO$_4$, and concentrated in vacuo. Silica gel chromatography provided 2 mg 53 (4%) and unreacted genipin. $^1$H NMR (400 MHz, CDCl$_3$) δ 7.53 (1H, s), 5.96 (1H, s), 4.47 (1H, d, J=12.4), 4.47 (1H, d, J=9.6 Hz), 3.71 (3H, s), 3.21 (1H, ddd, J=8.8, 8.8, 8.4,), 2.88 (1H, m), 2.56 (1H, dd, J=9.6, 7.6 Hz), 2.05 (1H, m).

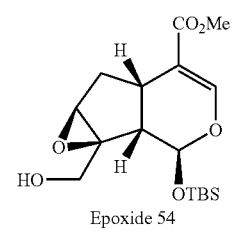

Epoxide 54

Allylic alcohol 49 (200 mg, 0.588 mmol), MCPBA (102 mg, 0.588 mmol) was dissolved in 3 mL of CH$_2$Cl$_2$ with a few drops of pH 7 buffer. The reaction was stirred at room temperature for 4 h. The reaction mixture was directly subjected to silica gel chromatography (hexane:EtOAc=3:1) to provide 54 as a white solid (158 mg, 75%). mp: 78-80° C.; $^1$H NMR (400 MHz, CDCl$_3$): δ 7.41 (s, 1H), 4.86 (d, J=9.2 Hz), 4.10 (d, J=11.6 Hz, 1H), 3.81 (1H, dd, J=11.6, 8.8 Hz), 3.70 (3H, s), 3.51 (1H, s), 2.79 (1H, ddd, J=8.8, 8.4, 8.4 Hz), 2.66 (1H, dd, J=14.0, 7.6 Hz), 2.35 (1H, dd, J=9.6, 7.2 Hz), 2.12 (1H, d, J=8.8 Hz), 1.36 (1H, dd, J=14.0, 10.0 Hz); $^{13}$C NMR (300 MHz, CDCl$_3$): δ 167.3, 151.7, 109.1, 94.5, 67.1, 60.5, 58.7, 51.1, 44.0, 34.0, 30.0, 25.5, 17.6, −4.2, −5.0. LRMS (CI reagent gas/NH$_3$): calcd. for [M+1]$^+$ C$_{17}$H$_{29}$O$_6$Si 357.2, found 357.3.

Compound 55

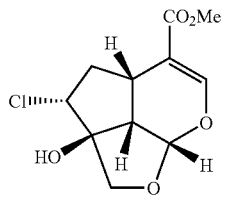

Compound 54 (20 mg, 0.0562 mmol) was dissolved in a 10 mL 1% mixture of HCl in EtOH. The reaction mixture was stirred at room temperature for 15 min. The solution was added 5% NaHCO$_3$, extracted with EtOAc, dried over Na$_2$SO$_4$, and concentrated in vacuo. Silica gel chromatography (hexane:EtOAc=3:1) provides 2 mg (15%) of 55. $^1$H NMR (400 MHz, CDCl$_3$) δ 7.48 (1H, s), 5.68 (1H, d, J=4.2 Hz), 4.38 (1H, d, J=10.4 Hz), 4.28 (1H, dd, J=6.4, 12.8 Hz), 3.74 (1H, s), 3.72 (3H, s), 3.01 (1H, m), 2.74 (1H, dt, J=6.4, 6.4 Hz), 2.60 (1H, dd, J=5.2, 10.4 Hz), 1.61 (1H, dd, J=9.3, 9.0 Hz).

Scheme XII: Other Derivatives that can be Employed as UCP Inhibitors.

The following compounds can be made by the synthetic methods taught herein.

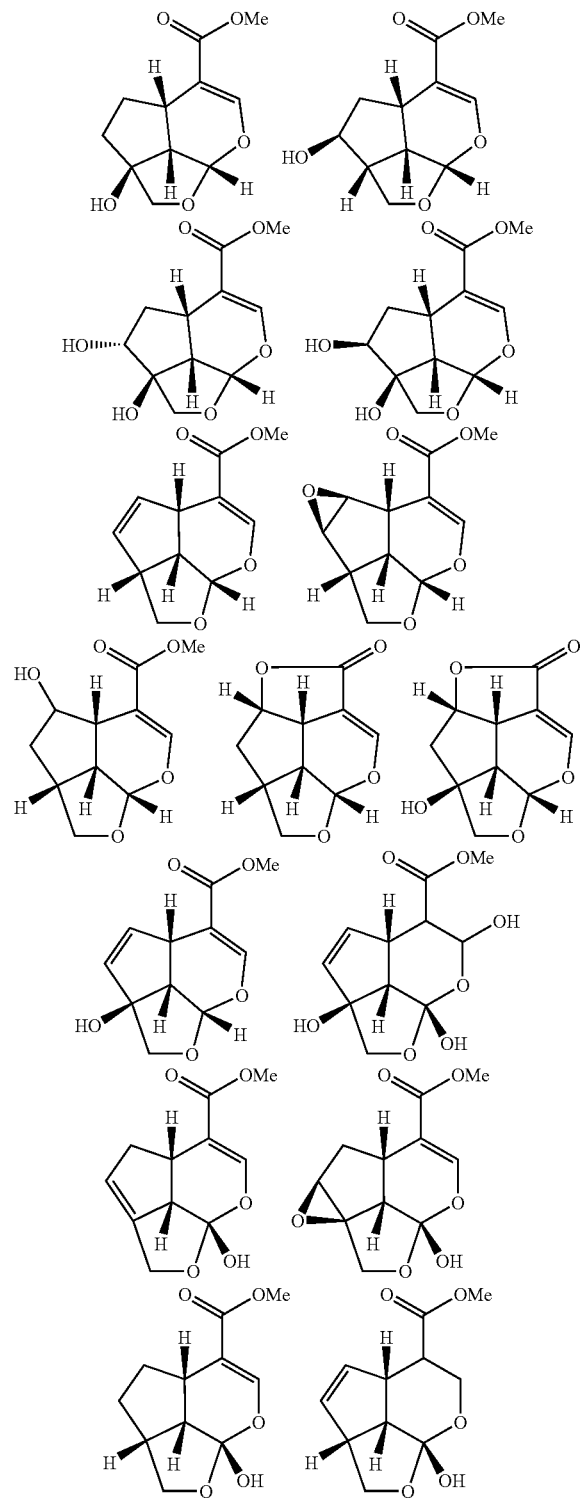

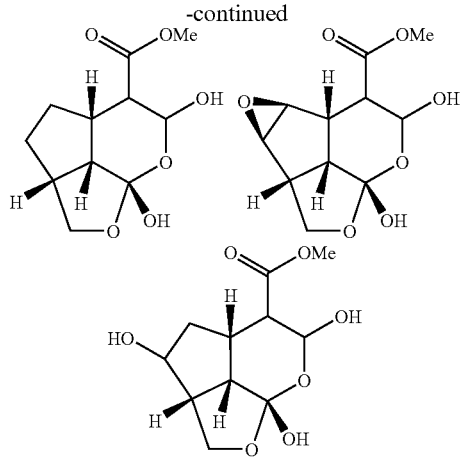

EXPERIMENTAL

I. Effect of Genipin on Superoxide-Activated, UCP2-Dependent Proton Leak

A. Isolation of Mitochondria

Wildtype and UCP2 knockout mice were used for isolation of kidney mitochondria. Fresh tissues were minced in ice-cold STE buffer (250 mM sucrose, 5 mM Tris, 2 mM EGTA, pH 7.4 at 4° C.), and disrupted in a Dounce homogenizer. Cell debris was removed by centrifugation of the homogenate at 500×g for 3 min. The supernatant was centrifuged at 10,000×g for 8 min., and the mitochondrial pellet was resuspended in ice-cold STE buffer. Mitochondria were subjected to another cycle of centrifugation at 750 and 10,000×g. Protein content was assayed using the bicinchoninic acid method.

B. Proton Leak Titrations in Mitochondria

Proton leak titration was performed in the presence of a superoxide-generating system (xanthine plus xanthine oxidase) essentially as described by Echtay, et al., *Nature* 2002, 415:96-99, the entire teachings of which are incorporated herein by reference.

Figure 2:
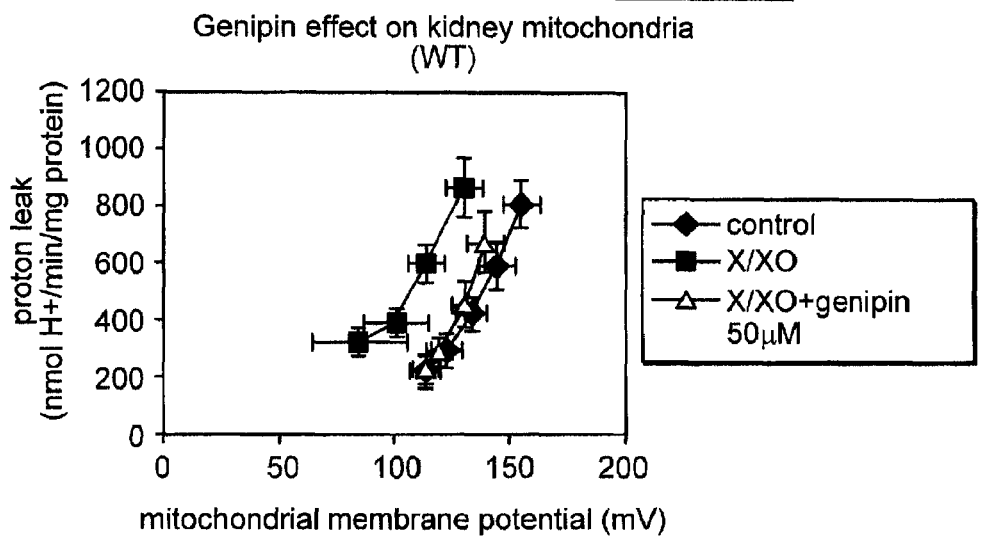
FIG. 2 is a graph showing the effect of genipin on superoxide-activated, UCP2-dependent proton leak in isolated kidney mitochondria of wild type mice.
Figure 3:
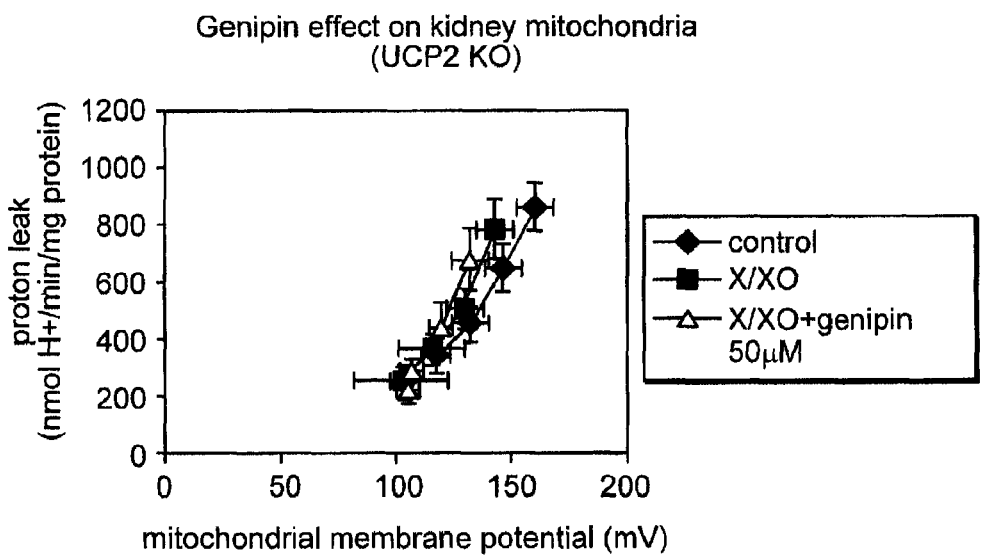
FIG. 3 is a graph showing the effect of genipin on superoxide-activated, UCP2-dependent proton leak in isolated kidney mitochondria of UCP2 knockout mice. Proton leak titration was performed in the presence of a superoxide-generating system (xanthine plus xanthine oxidase) essentially as described (Echtay et al. 2002, Nature 415, 96-99). Graphs show the rate of proton leak as a function of its driving force, mitochondrial membrane potential. ♦, control; ■, xanthine (50 mM) plus xanthine oxidase (0.2mU/3.5 ml). Δ, xanthine/xanthine oxidase plus 50 μM genipin. Mitochondria were incubated with genipin in the oxygen electrode for 5 minutes before xanthine oxidase was added (to initiate the generation of superoxide). Western-blot analysis confirmed that there was no UCP2 protein in mitochondria from UCP2 knockout mice. Data are means +/−S.E.M. of four independent experiments.

FIG. 2 shows the rate of proton leak as a function of its driving force, mitochondrial membrane potential, for kidney mitochondria of wildtype mice, whereas FIG. 3 shows the rate of proton leak as a function of mitochondrial membrane potential for kidney mitochondria of UCP2 knockout mice. In the control group, represented by solid diamonds in FIGS. 2 and 3, proton leak titration was performed in the absence of a superoxide-generating system. In the group represented by solid squares in FIGS. 2 and 3, proton leak titration was performed in the presence of the superoxide-generating system, 50 mM xanthine and 0.2 mU/3.5 mL xanthine oxidase. In the group represented by open triangles, the proton leak titration was performed in the presence of 50 mM xanthine, 0.2 mU/3.5 mL xanthine oxidase and 50 μM genipin.

As can be seen in FIG. 2, control kidney mitochondria of wildtype mice exhibited proton leakage at a higher mitochondria membrane potential than kidney mitochondria from wildtype mice that was exposed to the superoxide-generating system. However, when the mitochondria from wildtype mice was exposed to the superoxide-generating system in the presence of genipin, proton leak occurred at nearly the same mitochondria membrane potential as in the control.

To determine whether the increase in proton leak at lower mitochondrial membrane potentials observed when superoxide levels were increased was due to increased activity of UCP2, the same proton leak experiment was conducted with kidney mitochondria from mice lacking UCP2. UCP2 knockout mice were generated using the procedures described in U.S. Pat. No. 6,365,796, the entire teachings of which are incorporated herein by reference, and in Zhang, Chen-Yu, et al., *Cell* 2001, 105:745-755, the teachings of which are also incorporated herein by reference in their entirety. As can be seen in FIG. 3, kidney mitochondria from mice lacking UCP2 exposed to the superoxide-generating system, 50 mM xanthine and 0.2 mU/3.5 mL xanthine oxidase, exhibited almost the same proton leak vs. membrane potential curve as kidney mitochondria from control UCP2 knockout mice which were not exposed to the superoxide-generating system. This experiment provides evidence that increased levels of superoxide ions cause increased proton leak and lower membrane potentials by activating UCP2. When kidney mitochondria from UCP2 knockout mice were exposed to both the superoxide-generating system and 50 μM genipin, proton leak occurred at approximately the same membrane potential as that observed for kidney mitochondria from UCP2 knockout mice exposed to the superoxide-generating system alone. This experiment provides evidence that genipin increases the membrane potential at which proton leak occurs by inhibiting the activity of UCP2.

II. Effect of Genipin on Insulin Secretion in Pancreatic Islets From Wildtype and UCP2 Knockout Mice A. Isolation of Pancreatic Islets As used or herein, pancreatic islets from wildtype and UCP2 knockout mice were isolated according to a method used for rats (Cawthorn and Chan, Mol. Cell. Endocrinol. 1991, 75:197-204, the entire teachings of which are incorporated herein by reference), except that the total exposure to type XI collagenase (Worthington Biochemical Co., NJ) was 30 min. and the Ficoll gradient was altered to layers of 25%, 23%, 21%, and 11%. Islets were harvested from the 11%-21% interface.

B. Effect of Genipin on Insulin Secretion

Figure 4:
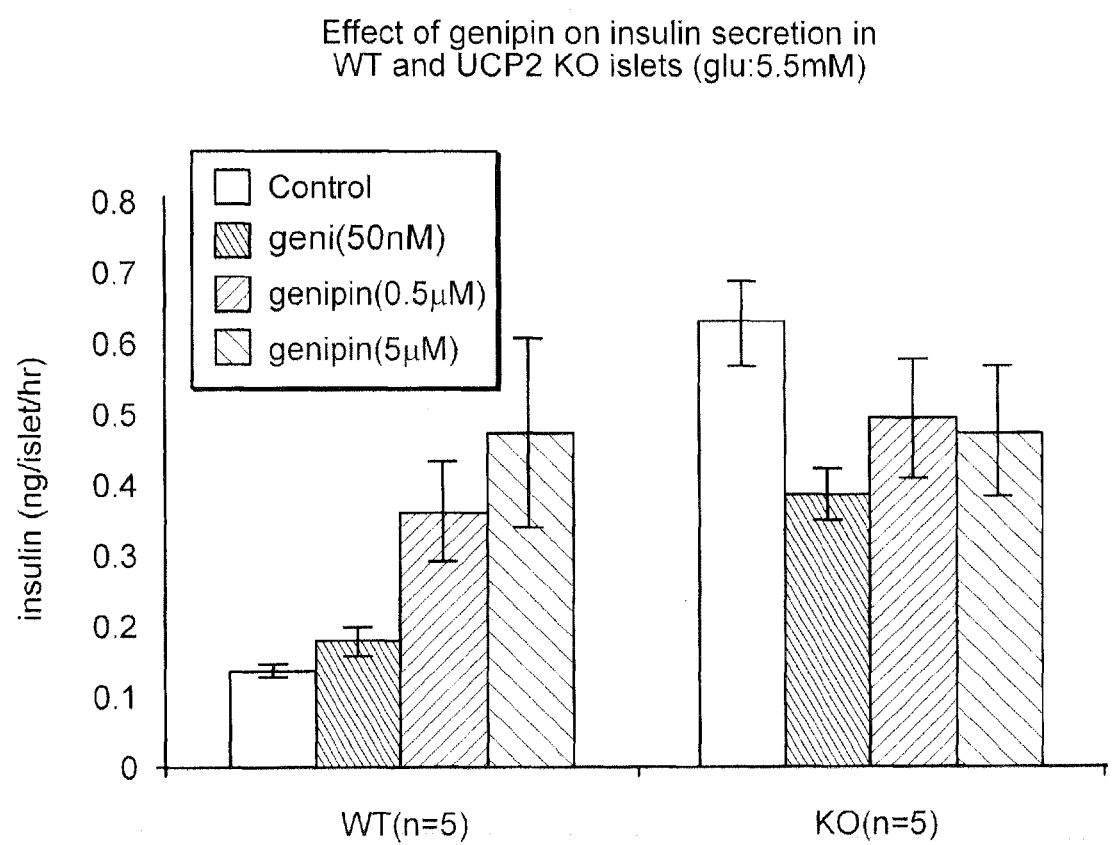
FIG. 4 is a graph comparing the effect of genipin on insulin secretion of pancreatic islets from wild type mice and UCP2 knockout mice in the presence of 5.5 mM of glucose.
Figure 5:
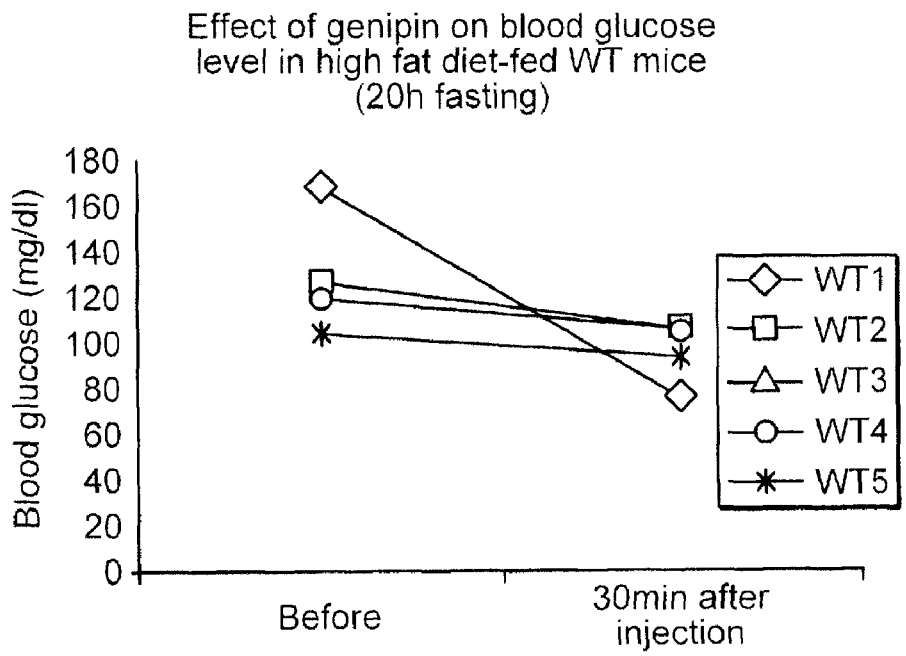
FIG. 5 is a graph showing the effect of an injection of genipin on blood glucose levels in wild type mice that have been feed a high fat diet.

Islets were cultured in RPMI medium containing 11.0 mM glucose and supplemented with 1% penicillin-streptomycin. 7.5% fetal bovine serum (all from Gibco/BRL, Burlington, ON), and 10 mM Hepes (Sigma). After culturing for 20-24 hr, the islets were transferred to microcentrifuge tubes, pelleted (800 g for 5 min), and the medium aspirated and replaced with 1.0 mL DME medium containing 1% gelatin and 5.5 mM glucose with no genipin (control), 50 nM genipin, 0.5 μM genipin, and 5 μM genipin. For insulin secretion studies, the three islets were incubated per tube. After incubation at 37° C. for 60 min., the islets were centrifuged. The supernatant was collected and stored at −80° C., and then later assayed for insulin using Rat Insulin ELISA Kit (Cat. No. INSKR020, Crystal Chem., Inc., Chicago, Ill.). The results shown in FIG. 4 demonstrate that pancreatic islets from UCP2 knockout mice exhibit greater insulin secretion than pancreatic islets from wildtype mice. In addition, the data in FIG. 4 demonstrates that genipin increases insulin secretion by pancreatic islets isolated from wildtype mice but does not increase insulin secretion by pancreatic islets isolated from UCP2 knockout mice. This indicates that genipin increases insulin secretion by inhibiting UCP2.

Figure 6:
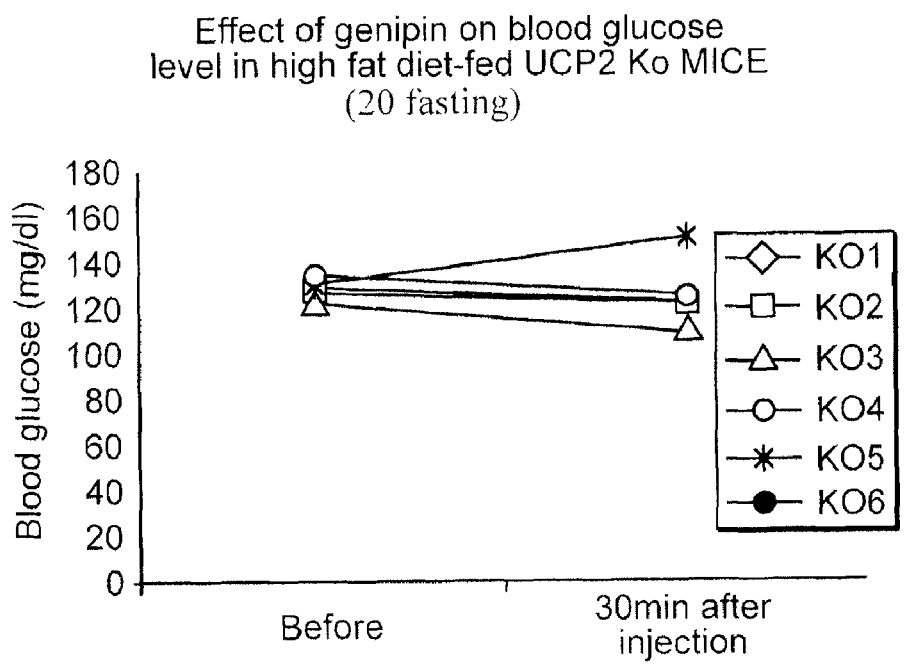
FIG. 6 is a graph showing the effect of an injection of genipin on blood glucose levels in UCP2 knockout mice that have been feed a high fat diet.
Figure 7:
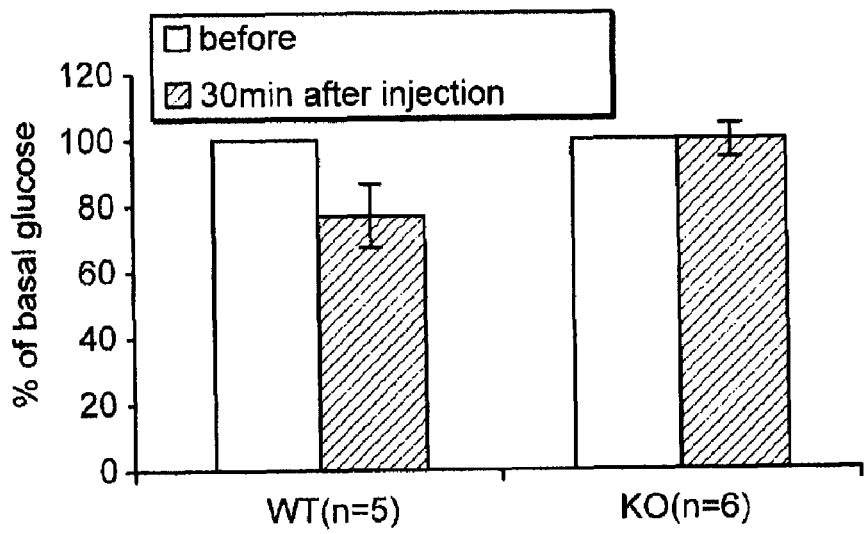
FIG. 7 is a graph comparing the effect of an injection of genipin on the blood glucose levels of wild type mice and UCP2 knockout mice that have been feed on a high fat diet.
Figure 8:
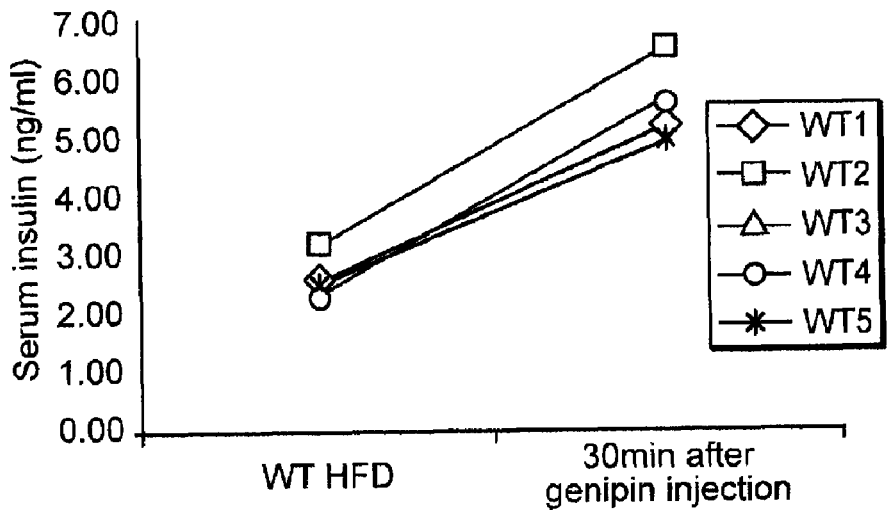
FIG. 8 is a graph showing the effect of an injection of genipin on insulin secretion in wild type mice that have been feed on a high fat diet.
Figure 9:
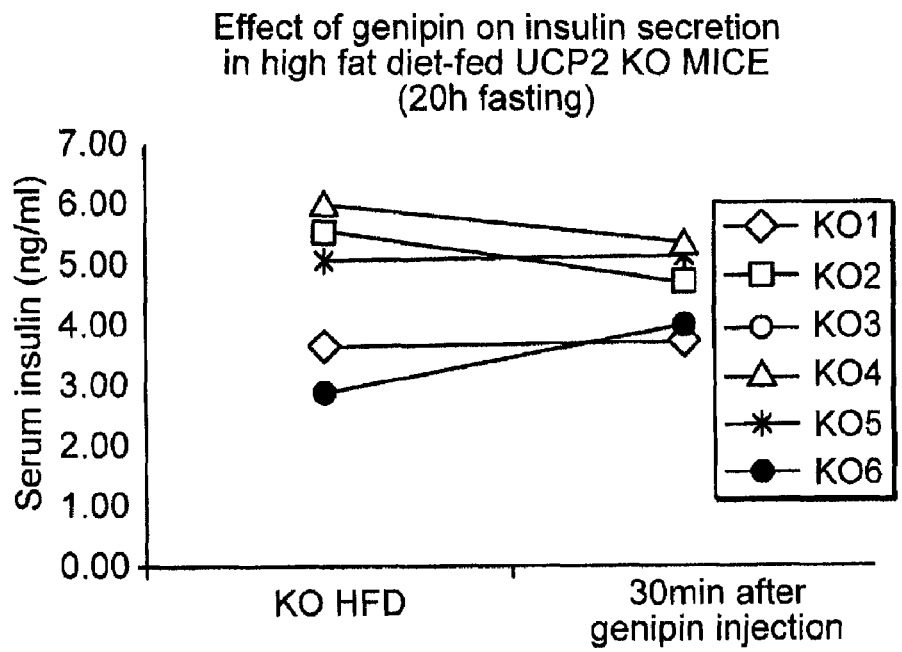
FIG. 9 is a graph showing the effect of an injection of genipin on insulin secretion in UCP2 knockout mice that have been feed on a high fat diet.
Figure 10:
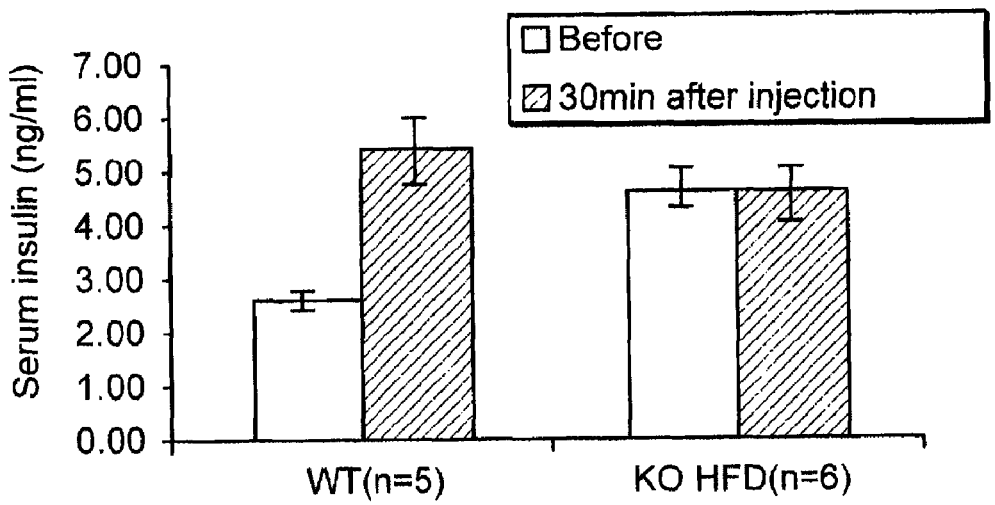
FIG. 10 is a graph comparing the effect of an injection of genipin on insulin secretion of wild type mice and UCP2 knockout mice that have been feed on a high fat diet.

III. Effect of Genipin on Blood Glucose Level and Insulin Secretion in High Fat Diet-Fed Wildtype and UCP2 Knockout Mice Wildtype and UCP2 knockout mice were placed on a high fat diet obtained from Research Diets Inc., New Brunswick, N.J. (cat. no. D12331, HFD). The fat source was coconut oil and comprised 58% of the total calories. The mice remained on the high fat diet for 24 weeks. After the 24 weeks, both the wildtype and the UCP2 knockout mice were obese (about 50-60 g). After 20 hours of fasting, the blood glucose and insulin levels of the mice were measured, then the mice were injected with 300 μg of genipin. Thirty minutes after injection the blood glucose and insulin levels of the mice were measured again. Blood glucose levels were assessed using a glucometer (One touch, Lifescan, Milpitas, Calif.). Serum insulin concentrations were assessed using mouse insulin as a standard (Rat Insulin ELISA Kit. cat. #INSKR020 Crystal Chem. Inc., Chicago, Ill.). Blood glucose levels of wildtype mice before and after injection with genipin, shown in FIG. 5, demonstrate that the genipin injection significantly lowered blood glucose. The injection of genipin also dramatically increase the blood insulin levels of wildtype mice, as can be seen in FIG. 8. In contrast, an injection of genipin had little effect on either blood glucose or insulin levels in UCP2 knockout mice, as can be seen in FIGS. 6 and 9, respectively. A comparison of the effect of genipin on the blood glucose levels and insulin levels in wildtype and UCP2 knockout mice can be seen in FIGS. 7 and 10, respectively. The data in FIGS. 5-10 provides strong evidence that genipin increases insulin secretion and decreases blood sugar in mammals by inhibiting the activity of UCP2.

IV. Crosslinking in Genipin Versus Non-Crosslinking in Certain Genipin Derivatives Genipin (Scheme XIII), a well-known naturally occurring cross-linking agent (see, for example, Fujikawa, S.; Nakamura, S.; Koga, K. *Agric. Biol. Chem.* 1988, 52, 869; and Huang, L. L.; Sung, H. W.; Tsai, C. C.; Huang, D. M. *Journal of Biomedical Materials Research*, 1998, 42, 568; the entire teachings of which are incorporated herein by reference) forms a dark blue pigment upon treatment with primary amines, amino acids, and peptides. Model chemical reactivity studies (Fujikawa, S.; Fukui, Y.; Koga, K. *Tetrahedron Lett.* 1987, 28, 4699, the entire teachings of which are incorporated herein by reference) have shown that the pseudo-crosslinked blue pigment genipocyanin G is produced when genipin is treated with glycine at 80° C. (Scheme XIII). It has also been proposed (Touyama, R.; Inoue, K.; Takeda, Y.; Yatsuzuka, M.; Ikumoto, T.; Moritome, N.; Shingu, T.; Yoloi, T.; Inouye, H. *Chem. Pharm. Bull.* 1994, 42, 1571) a crosslinking mechanism to form the dimeric pigment 56 when genipin was treated with methylamine (Scheme XIV). These studies show that genipin can dimerize in the presence of nucleophiles such as primary amines and that the C7-C8 double bond and the C10 primary alcohol of genipin are necessary for the crosslinking process.

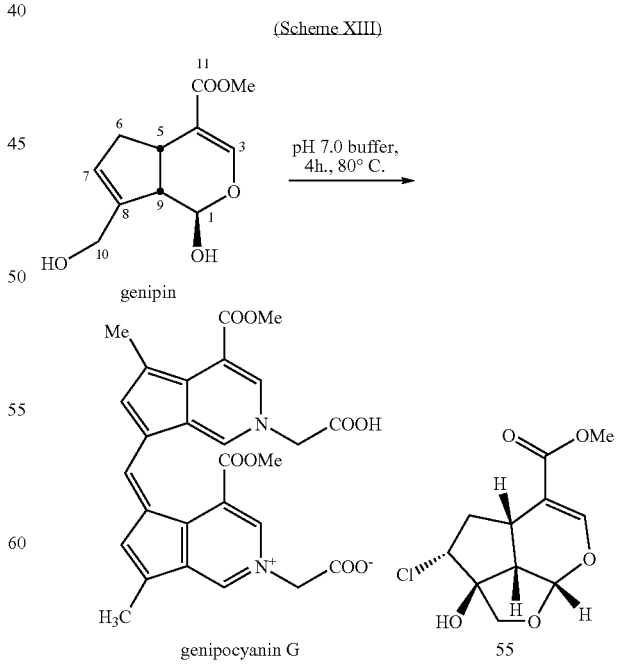

(Scheme XIV)
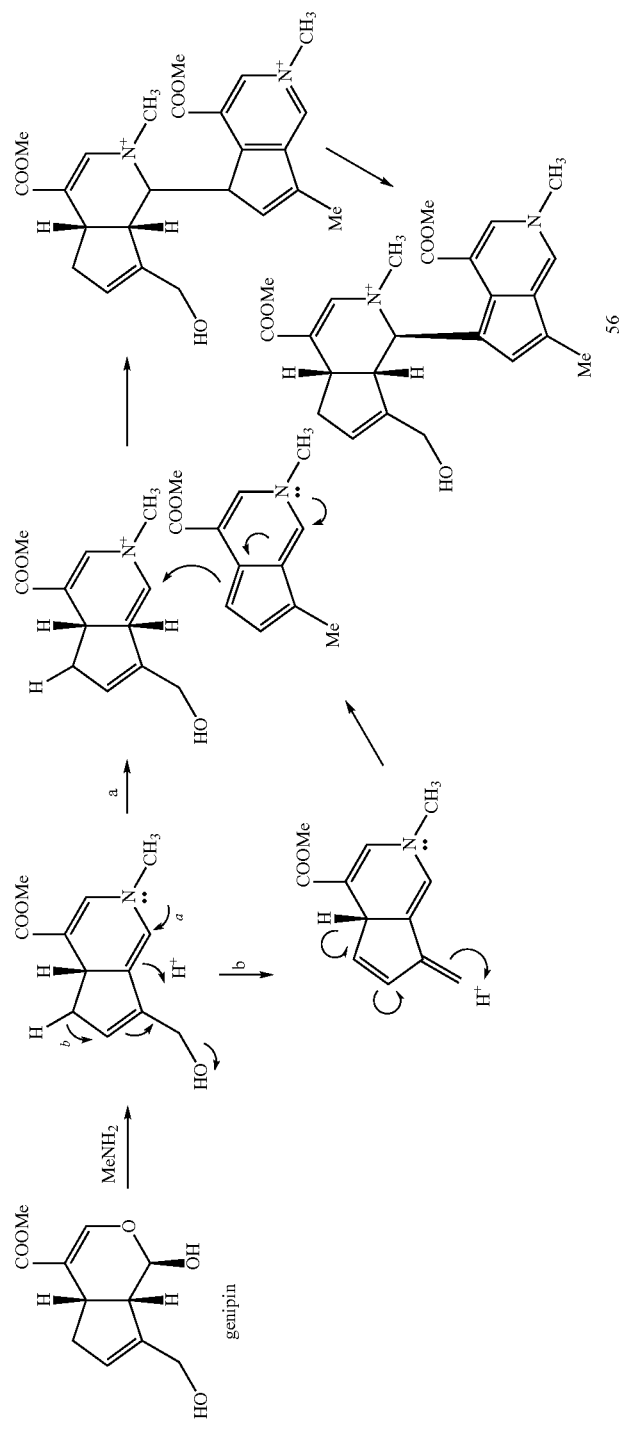

Certain genipin derivatives lacking these two active sites (e.g. compound 55) can lose crosslinking activity when treated with amine nucleophiles. This can be shown using methods known to one skilled in the art. In one embodiment, a simple comparative color assay can be used wherein genipin and a derivative, e.g., compound 55, are treated with glycine. Both genipin and compound 55 were dissolved in pH 7 buffer and mixed with an equimolar amount of glycine at 80° C. After 4 hours, the genipin solution turned dark blue indicating formation of genipocyanin and other colored pigments, while the compound 55 solution was still clear, which indicates the crosslinking process to form highly conjugated blue dyes did not occur under these conditions with compound 55.

Figure 11A:
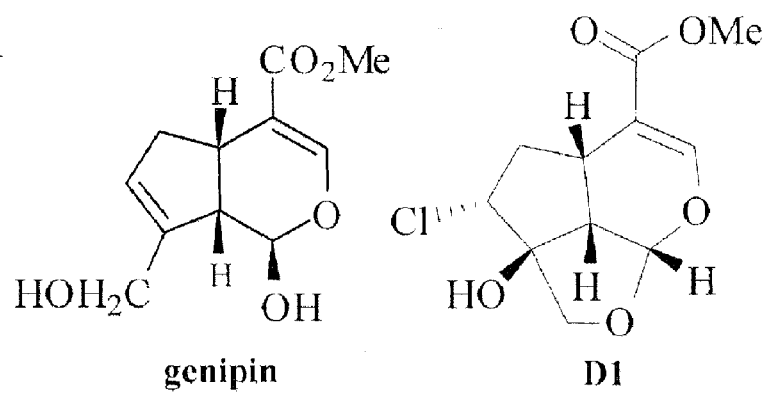
FIG. 11A shows structures of genipin and its derivative D1 (compound 55).
Figure 11B:
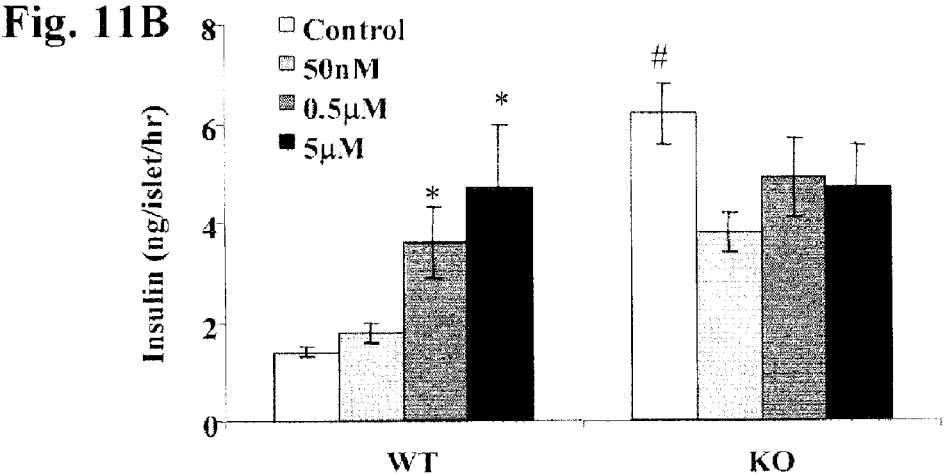
FIGS. 11B and 11C are bar graphs showing effects of genipin and D1, respectively, on insulin secretion in isolated islets obtained from wild type and UCP2 knockout mice.
Figure 11C:
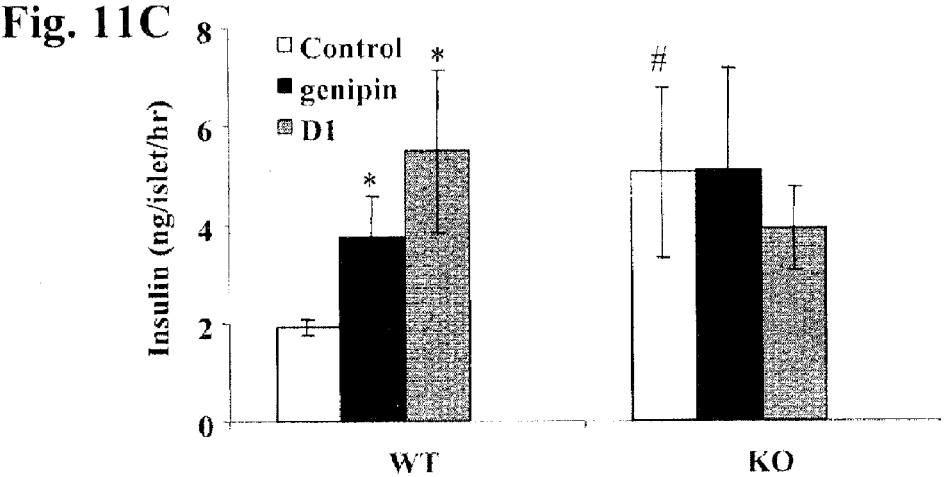

V. Effects of Hyperglycemia and Obesity on β-Cell Dysfunction in Wild Type (WT) and UCP2-Deficient Islets, with or without 5 µM Genipin FIG. 11A shows the structure of genipin and its derivative D1 (compound 55). FIGS. 11B and 11C show their effects on insulin secretion. Pancreatic islets were isolated from WT or UCP2 knockout (KO) mice. Islets were cultured in RPMI medium containing 11.0 mM glucose and supplemented with 1% penicillin/streptomycin, 7.5% fetal bovine serum (all from Gibco/BRL, Burlington, ON) and 10 mM Hepes (Sigma). After overnight preincubation, the islets were transferred to microcentrifuge tubes, and pelleted (800 g for 5 min). The medium was aspirated and replaced with 1.0 mL DME medium containing 0.1% gelatin and 5.5 mM glucose with 50 nM, 0.5 µM and 5 µM genipin (FIG. 11B), or 5 µM genipin or D1 (FIG. 11C). For insulin secretion studies, three islets were incubated per tube. After incubation at 37° C. for 60 min, the islets were centrifuged as before. The supernatant was collected and stored at −80° C., and then later assayed for insulin using a Rat Insulin ELISA Kit (Cat # INSKR020, Crystal Chem. Inc., Chicago, Ill.).

FIG. 11B shows that genipin increases insulin secretion in a dose-dependent manner in WT islets. UCP2-deficient islets had increased insulin secretion as previously observed. However, genipin had no effect on insulin secretion in UCP2-deficient islets. FIG. 11C shows that genipin's derivative D1 increases insulin secretion in WT islets, but not in UCP2 KO islets.

Genipin is a known naturally occurring cross-linking agent. It has been shown that genipin can dimerize in the presence of nucleophiles such as primary amines and that the C7-C8 double bond and the C10 primary alcohol of genipin are necessary for the crosslinking process. As shown herein (see Example IV, above) a genipin derivative lacking these two active sites (e.g. D1) has no crosslinking activity.

Thus, genipin can inhibit UCP2 activity, thus, increasing insulin secretion. Genipin's cross-linking activity does not appear to be relevant to its UCP2 inhibitory activity, so derivatives such as D1 (compound 55) can be effective UCP2 inhibitors without the crosslinking activity of genipin.

VI. Effect of Hyperglycemia and Obesity on In Vitro Cell Dysfunction in WT and UCP2-Deficient Islets, with or without 5 µM Genipin A large body of work has established that chronic hyperglycemia- and obesity-mediated loss of glucose-stimulated insulin secretion (GSIS), e.g., impaired secretion of insulin by pancreatic β-cells, together with resistance to insulin action, is a causative factor for type 2 diabetes. We have shown that lack of a UCP2 gene or removal of endogenously produced superoxide (a UCP2 activator) improved loss of GSIS caused by hyperglycemia and obesity. In the present study, we have assessed the effect of genipin on hyperglycemia- and obesity-induced β-cell dysfunction.

Pancreatic islets were isolated from WT (FIG. 12A) or UCP2 KO mice (FIG. 12B) and subjected to chronic incubations at low (5.5 mM) and high glucose (25 mM). In a separate experiment, islets were isolated from ob/ob mice (FIG. 12C). Islets were incubated for a total of 72 hours and washed, and then insulin-secretion studies were performed using three different concentrations of glucose (5.5, 12.5, and 25 mM) with or without 5 µM genipin. Results are means±SEM of four independent experiments (FIGS. 12A and 12B) or eight to twenty repeats of one representative experiment (FIG. 12C). WT islets that were chronically incubated at low glucose released increasing amounts of insulin in response to increasing concentrations of glucose (FIG. 12A, left panel). Following chronic hyperglycemia, islets increased basal insulin release, but were completely unresponsive to glucose stimulation (FIG. 12A, middle panel). These data are consistent with other reports showing that chronic hyperglycemia increases basal insulin secretion, and, at the same time, causes complete loss of glucose responsiveness. To assess the role of genipin in hyperglycemia-induced loss of glucose responsiveness, genipin was acutely added into islets during the insulin-release phase of the study. Acutely added genipin prevented the hyperglycemia-induced block in GSIS (FIG. 12A, right panel).

To see whether this effect of genipin is mediated by UCP2, islets were isolated from UCP2 KO mice and then incubated in chronic hyperglycemia. Following chronic incubation in low glucose (5.5 mM), UCP2 KO islets, like WT islets, released increasing amounts of insulin in response to increasing concentrations of glucose (FIG. 12B, left panel). Consistent with the inhibitory effect of UCP2 on insulin secretion, levels of insulin secretion were higher than those observed in WT islets (FIG. 12A, left panel). However, unlike WT islets, islets from UCP2 KO mice, when incubated at 25 mM glucose, retained glucose responsiveness (FIG. 12B, middle panel). Their pattern of response was similar to that observed in WT islets incubated with genipin (FIG. 12A, middle panel). Importantly, in UCP2 KO islets, genipin had no additional beneficial effect on GSIS (FIG. 12B, right panel), indicating that genipin improves chronic hyperglycemia-induced loss of glucose responsiveness by inhibiting UCP2.

Insulin secretion in islets from ob/ob mice and ob/ob mice lacking UCP2 with or without genipin was also studied. It has been reported that in ob/ob islets, UCP2 expression levels are increased compared to WT islets. Islets from ob/ob mice showed elevated basal insulin secretion and loss of glucose responsiveness compared to WT islets (FIG. 12C, far left panel vs. FIG. 12A, left panel), similar to what was observed in WT islets following chronic hyperglycemia (FIG. 12A, middle panel). Acutely adding genipin restored glucose sensing in ob/ob islets (FIG. 12C, second panel from left). Islets isolated from ob/ob mice lacking UCP2 also had restored GSIS (FIG. 12C, second panel from right), similar to ob/ob islets treated with genipin, and also similar to WT islets treated with genipin (FIG. 12A, right panel), or UCP2 deficient islets during exposure to hyperglycemia (FIG. 12B, middle panel). Of note, genipin treatment of islets from ob/ob mice lacking UCP2 did not improve glucose sensing above the level seen in islets lacking UCP2 alone (FIG. 12C, right panel).

These data demonstrate that genipin can inhibit UCP2 activity, and improve hyperglycemia- and obesity-mediated β-cell dysfunction in vitro.

VII. Effect of Genipin on Insulin Secretion In Vivo

UCP2-deficient mice have increased serum insulin levels. Genipin inhibits UCP2 activity, and thus should stimulate insulin secretion acutely in vivo. In the present study, the effect of genipin on insulin secretion in vivo was assessed. WT and UCP2 KO mice were fed a chow diet (FIG. 13A), or placed on a high fat diet (HFD) (FIG. 13B) (#D12331, obtained from Research Diets Inc., New Brunswick, N.J.). The fat source was coconut oil and comprised 58% of the total calories. The mice remained on the HFD for 24 weeks. Both WT and KO mice were obese (50-60 g). ob/ob mice (FIG. 13C) were obtained from The Jackson Laboratory. After 6 hours (FIG. 13A) or 20 hours (FIGS. 13B and 13C) of fasting, genipin (10 mg/kg (FIGS. 13A and 13B), or 20 mg/kg (FIG. 13C)) was injected into the mice. Serum insulin levels were measured before and after administration of genipin as indicated. As shown, genipin can increase insulin levels in all three animal models (FIGS. 13A-C). Importantly, genipin has no effect on insulin levels in UCP2 KO mice. These data demonstrate that genipin can increase insulin levels in vivo by inhibiting UCP2.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a disorder selected from deficient first-phase insulin secretion, non-insulin dependent diabetes mellitus, or a combination of deficient first-phase insulin secretion and non-insulin dependent diabetes mellitus in a mammal, comprising:

i) administering to the mammal a compound represented by the following structural formula:

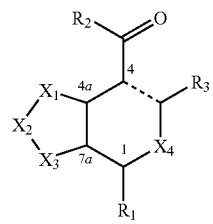

or pharmaceutically acceptable salts thereof, wherein:
———— is a single or double bond;
$X_1$ is $=CR_{18}-$, $X_2$ is $=CR_{12}-$, and $X_3$ is $CR_{13}R_{14}$; $X_2$ is $=CR_{18}-$, $X_3$ is $=CR_{12}-$, and $X_1$ is $CR_{13}R_{14}$; or $X_1$ is $CR_6R_7$, $X_2$ is $CR_8R_9$ and $X_3$ is $CR_{10}R_{11}$;
$X_4$ is $-O-$ or $-NR'-$;
R' is H or a C1-C5 alkyl;
$R_1$ is $-H$, $-OH$, $=O$, $-OSi(R_{19})_3$, a hexose or pentose; or $R_1$, taken together with a substituent of $X_3$ selected from $R_{10}, R_{11}, R_{12}, R_{13}, R_{14},$ and $R_{18}$, together with C7a, the carbon to which $R_1$ is attached, and the carbon represented by $X_3$, form a cyclic ether;
$R_2$ is $-OR$, or $-NR_4R_5$; or when $X_1$ is $CR_{13}R_{14}$, $R_2$ and $R_{13}$, together with C4, C4a, the carbon to which $R_{13}$ is attached and the carbonyl group to which $R_2$ is attached, form a lactone ring;
R is H or a C1-C5 alkyl;
$R_3$ is $-H$, $-OH$, or $-OR$, or, optionally when ———— is a single bond, $=O$;
$R_4$ and $R_5$ are each, independently, $-H$ or a C1-C5 alkyl; or $R_4$ and $R_5$ together with the nitrogen to which they are attached form a heterocyclic ring, wherein the C1-C5 alkyl or the heterocyclic ring are optionally substituted with one or more of hydroxy, a halo, a C1-C5 alkyl, phenyl, or cyano;
$R_6, R_7, R_8, R_9, R_{10}, R_{11}, R_{13}, R_{14}$ and $R_{99}$ are independently $-H$, $-OH$, $-F$, $-Cl$, $-Br$, $-I$, $-NO_2$, $-NR_2$, $-C(O)NR_2$, a C1-C5 alkyl, a hydroxyalkyl, $-CH_2OC(O)NR_{15}R_{16}$, or $-CH_2OC(O)R_{17}$; or $R_{13}$ and $R_{14}$ together are $=O$; or $R_8$ and $R_{10}$ together with two adjacent carbons to which they are attached, form an epoxy ring; or $R_6$ and $R_8$ together with two adjacent carbons to which they are attached, form an epoxy ring;
$R_{12}$ and $R_{18}$ are each, independently, $-H$, a C1-C5 alkyl, hydroxyalkyl, $-CH_2OC(O)NR_{15}R_{16}$, $-CH_2OC(O)R_{17}$, or $-CH_2OH$;
$R_{15}$ and $R_{16}$ are each, independently, $-H$ or a C1-C5 alkyl;
$R_{17}$ is a C1-C5 alkyl; and
$R_{19}$ for each occurrence is, independently, a C1-C5 alkyl or an aryl, provided that
when $X_4$ is $-O-$, $R_2$ is $-OCH_3$, and $R_1$ is $=O$, $-OH$, $-OC(O)CH_3$, glucosyl, O-tetraacetylglucosyl, O-tetramethylglucosyl, or t-butyldimethylsiloxy, and $X_3$ is $=CR_{12}$ or $CR_{10}R_{11}$, then none of $R_{10}, R_{11}$, or $R_{12}$ is $-CH_2OH$, $-CH_2OC(O)CH_3$, or $-CH_3$;
when $X_4$ is $-O-$, $R_2$ is $-OCH_3$, and $R_1$ is $-H$, $=O$, $-OH$ or t-butyldimethylsiloxy, and $X_3$ is $CR_{10}R_{11}$, then none of $R_{10}$ and $R_{11}$ is $-CH_2OH$, and $R_{10}$ and $R_{11}$ are not both $-H$; and
the compound is not

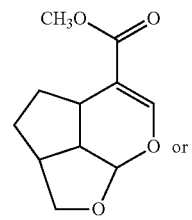

ii) administering to the mammal a compound represented a structural formula selected from:

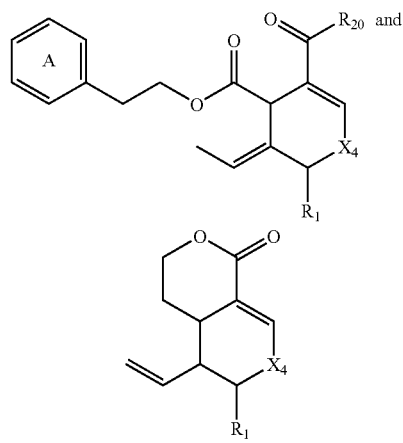

or pharmaceutically acceptable salts thereof, wherein:
ring A is optionally substituted with one or more of $-OH$, a halo, nitro, cyano, or carboxy;
$X_4$ is $-O-$ or $-NR-$;
R is H or a C1-C5 alkyl;

$R_1$ is —OH, =O, —OSi$(R_{19})_3$, a hexose or pentose;
$R_{20}$ is —OR, or —NR$_4$R$_5$; and
$R_4$ and $R_5$ are each, independently, —H or a C1-C5 alkyl; or $R_4$ and $R_5$ together with the nitrogen to which they are attached form a heterocyclic ring, wherein the C1-C5 alkyl or the heterocyclic ring are optionally substituted with one or more of hydroxy, a halo, a C1-C5 alkyl, phenyl, or cyano.

2. The method of claim 1, wherein the compound is represented by the following structural formula:

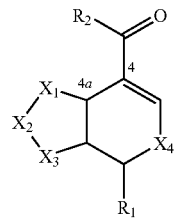

wherein:

$X_1$ is =CR$_{18}$—, $X_2$ is =CR$_{12}$—, and $X_3$ is CR$_{13}$R$_{14}$; $X_2$ is =CR$_{18}$—, $X_3$ is =CR$_{12}$—, and $X_1$ is CR$_{13}$R$_{14}$; or $X_1$ is CR$_6$R$_7$, $X_2$ is CR$_8$R$_9$ and $X_3$ is CR$_{10}$R$_{11}$;

$X_4$ is —O— or —NR—;

R is H or a C1-C5 alkyl;

$R_1$ is —OH, =O, —OSi$(R_{19})_3$, a hexose or pentose;

$R_2$ is —OR, or —NR$_4$R$_5$; or when $X_1$ is CR$_{13}$R$_{14}$, $R_2$ and $R_{13}$, together with C4, C4a, C5, the carbon to which $R_{13}$ is attached and the carbonyl group to which $R_2$ is attached, form a five membered lactone ring;

$R_4$ and $R_5$ are each, independently, —H or a C1-C5 alkyl; or $R_4$ and $R_5$ together with the nitrogen to which they are attached form a heterocyclic ring, wherein the C1-C5 alkyl or the heterocyclic ring are optionally substituted with one or more of hydroxy, a halo, a C1-C5 alkyl, phenyl, or cyano;

$R_6$, $R_7$, $R_8$, $R_9$, $R_{10}$, $R_{11}$, $R_{13}$ and $R_{14}$ are independently —H, —OH, a C1-C5 alkyl, a hydroxyalkyl, —CH$_2$OC(O)NR$_{15}$R$_{16}$, —CH$_2$OC(O)R$_{17}$, or —CH$_2$OH; or $R_{13}$ and $R_{14}$ together are =O; or $R_8$ and $R_{10}$ together with two adjacent carbons to which they are attached, form an epoxy ring;

$R_{12}$ and $R_{18}$ are each, independently, —H, a C1-C5 alkyl, hydroxyalkyl, —CH$_2$OC(O)NR$_{15}$R$_{16}$, —CH$_2$OC(O)R$_{17}$, or —CH$_2$OH;

$R_{15}$ and $R_{16}$ are each, independently, —H or a C1-C5 alkyl;

$R_{17}$ is a C1-C5 alkyl; and $R_{19}$ for each occurrence is, independently, a C1-C5 alkyl or an aryl.

3. The method of claim 1, wherein the compound is represented by the following structural formula:

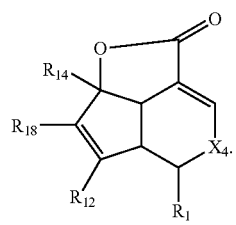

4. The method of claim 1, wherein the compound is represented by the following structural formula:

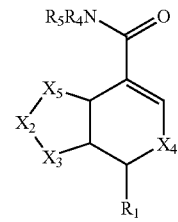

wherein:

$X_5$ is =CR$_{18}$—, $X_2$ is =CR$_{12}$—, and $X_3$ is CR$_{13}$R$_{14}$; $X_2$ is =CR$_{18}$—, $X_3$ is =CR$_{12}$—, and $X_5$ is CR$_{21}$R$_{22}$; or $X_1$ is CR$_6$R$_7$, $X_2$ is CR$_8$R$_9$ and $X_3$ is CR$_{10}$R$_{11}$; and $R_{21}$ and $R_{22}$ are independently —H, —OH, a C1-C5 alkyl, a hydroxyalkyl, —CH$_2$OC(O)NR$_{15}$R$_{16}$, —CH$_2$OC(O)R$_{17}$, or —CH$_2$OH; or $R_{21}$ and $R_{22}$ together are =O.

5. The method of claim 1, wherein the compound is represented by the following structural formula:

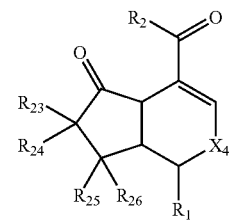

wherein:

$R_2$ is —OR, or —NR$_4$R$_5$; and $R_{23}$, $R_{24}$, $R_{25}$, $R_{26}$ are independently —H, —OH, a C1-C5 alkyl, a hydroxyalkyl, —CH$_2$OC(O)NR$_{15}$R$_{16}$, —CH$_2$OC(O)R$_{17}$, or —CH$_2$OH, provided that when $R_1$ is glucosyl and $R_{25}$ is —H, $R_{26}$ is not methyl.

6. The method of claim 2, wherein the non-insulin dependent diabetes mellitus is the early stages of non-insulin dependent diabetes mellitus.

7. The method of claim 1, wherein the compound is represented by a structural formula selected from:

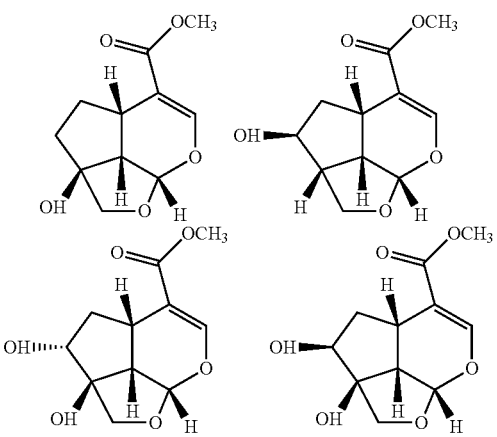

-continued

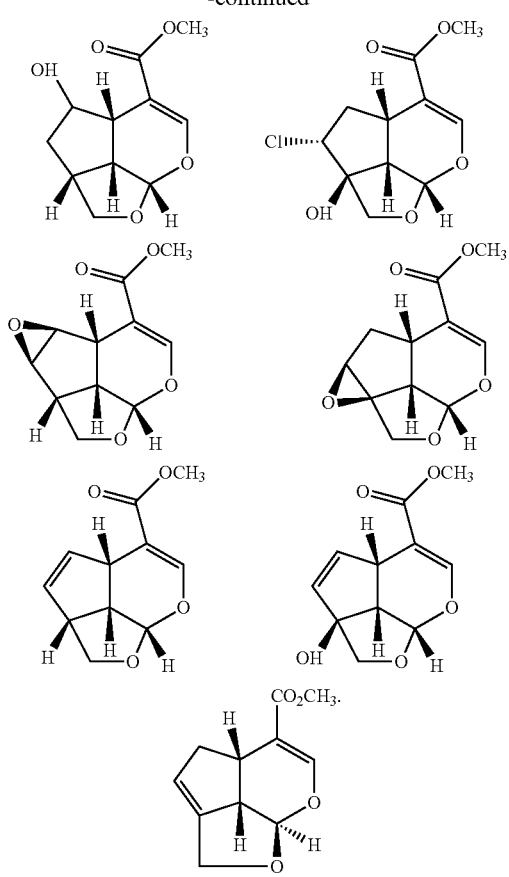

8. The method of claim 1, wherein the compound is represented by a structural formula selected from

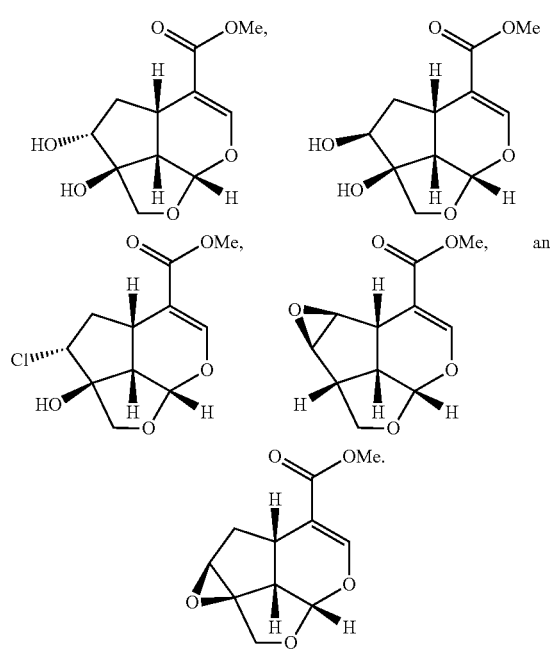

9. The method of claim 1, wherein the compound is represented by the following structural formula:

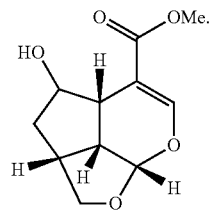

10. The method of claim 1, wherein the compound is represented by the following structural formula:

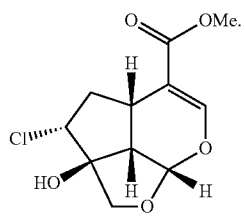

11. The method of claim 1, wherein the compound is represented by the following structural formula:

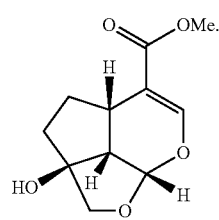

12. A method of treating a disorder selected from deficient first-phase insulin secretion, non-insulin dependent diabetes mellitus, or a combination of deficient first-phase insulin secretion and non-insulin dependent diabetes mellitus in a mammal, comprising administering to the mammal a compound represented by:

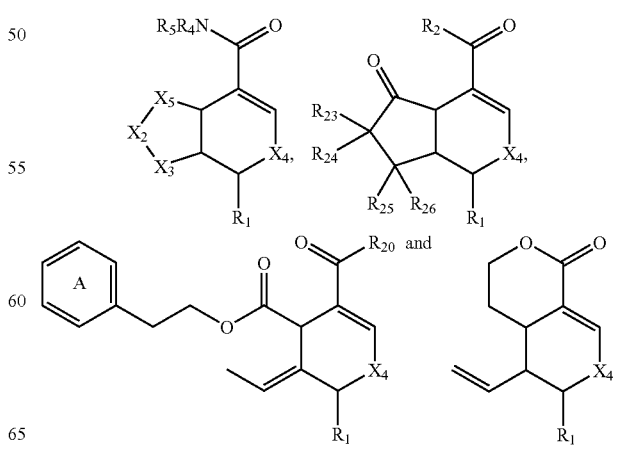

or pharmaceutically acceptable salts thereof, wherein:

———— is a single or double bond;

$X_1$ is $CR_6R_7$, $X_2$ is $CR_8R_9$ and $X_3$ is $CR_{10}R_{11}$;

$X_4$ is —O—;

$R_1$ taken together with a substituent of $X_3$ selected from $R_{10}$, $R_{11}$, together with C7a, the carbon to which $R_1$ is attached, and the carbon represented by $X_3$, form a cyclic ether; and $R_2$ is —OR or —$NR_4R_5$;

R is independently H or a C1-C5 alkyl;

$R_3$ is —H, —OH, or —OR, or, optionally when ———— is a single bond, =O;

$R_4$ and $R_5$ are each, independently, —H or a C1-C5 alkyl; or $R_4$ and $R_5$ together with the nitrogen to which they are attached form a heterocyclic ring, wherein the C1-C5 alkyl or the heterocyclic ring are optionally substituted with one or more of hydroxy, a halo, a C1-C5 alkyl, phenyl, or cyano;

$R_6$, $R_7$, and $R_{10}$ are independently selected from the group consisting of —H, —OH, —F, —Cl, —Br, —I, —$NO_2$, —$NR_2$, —C(O)$NR_2$, a C1-C5 alkyl, a hydroxyalkyl, —$CH_2OC(O)NR_{15}R_{16}$, and —$CH_2OC(O)R_{17}$; or $R_8$ and $R_{10}$ together with two adjacent carbons to which they are attached, form an epoxy ring; or $R_6$ and $R_8$ together with two adjacent carbons to which they are attached, form an epoxy ring;

$R_8$, $R_9$ and $R_{11}$ are independently selected from the group consisting of —H, —OH, —F, —Cl, —Br, —I, a C1-C5 alkyl and a hydroxyalkyl;

$R_{15}$ and $R_{16}$ are each, independently, —H or a C1-C5 alkyl; and $R_{17}$ is a C1-C5 alkyl, provided that the compound is not

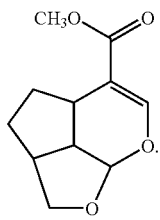

13. A method of treating a disorder selected from deficient first-phase insulin secretion, non-insulin dependent diabetes mellitus, or a combination of deficient first-phase insulin secretion and non-insulin dependent diabetes mellitus in a mammal, comprising administering to the mammal a compound represented by a structural formula selected from:

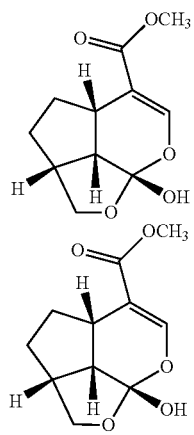 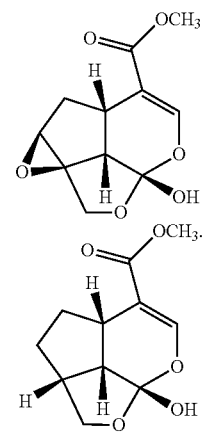

14. The method of claim 13, wherein the compound is represented by a compound represented by a structural formula selected from:

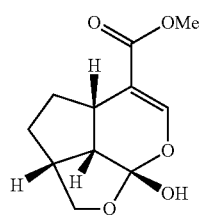 and 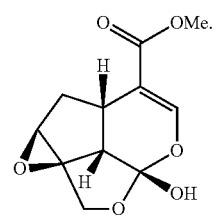

* * * * *

UNITED STATES PATENT AND TRADEMARK OFFICE
CERTIFICATE OF CORRECTION

PATENT NO. : 8,093,288 B2  Page 1 of 1
APPLICATION NO. : 12/622296
DATED : January 10, 2012
INVENTOR(S) : Chen-Yu Zhang et al.

It is certified that error appears in the above-identified patent and that said Letters Patent is hereby corrected as shown below:

In the Claims:

In Claim 12, column 48, lines 48-65, please delete the 4 chemical compounds and insert -- 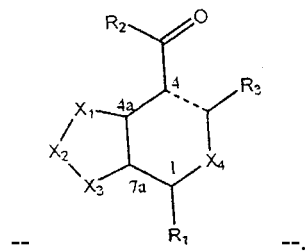 --.

In Claim 12, column 49, line 1, please delete "phar maceutically" and insert -- pharmaceutically --.

In Claim 13, column 50, lines 7-24, please delete the 4th chemical compound and insert -- 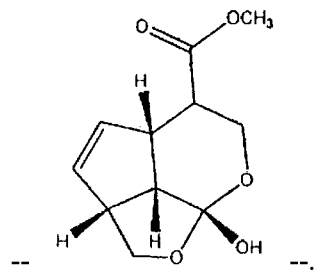 --.

Signed and Sealed this
Twenty-third Day of July, 2013

Teresa Stanek Rea
*Acting Director of the United States Patent and Trademark Office*